United States Patent [19]
Ishii et al.

[11] Patent Number: 5,749,363
[45] Date of Patent: May 12, 1998

[54] OSTEOPOROSIS DIAGNOSING APPARATUS AND METHOD

[75] Inventors: Tetsuya Ishii; Masashi Kuriwaki; Yasuyuki Kubota, all of Kyoto, Japan

[73] Assignee: Sekisui Kagaku Kogyo Kabushiki Kaisya, Osaka, Japan

[21] Appl. No.: 687,440

[22] PCT Filed: Dec. 14, 1995

[86] PCT No.: PCT/JP95/02569

§ 371 Date: Oct. 21, 1996

§ 102(e) Date: Oct. 21, 1996

[87] PCT Pub. No.: WO96/18342

PCT Pub. Date: Jun. 20, 1996

[30] Foreign Application Priority Data

| Dec. 14, 1994 | [JP] | Japan | 6-310445 |
| Jun. 7, 1995 | [JP] | Japan | 7-140730 |
| Jun. 7, 1995 | [JP] | Japan | 7-140731 |
| Jun. 7, 1995 | [JP] | Japan | 7-140732 |
| Jun. 7, 1995 | [JP] | Japan | 7-140733 |
| Jun. 7, 1995 | [JP] | Japan | 7-140734 |

[51] Int. Cl.⁶ ............................................. A61B 8/00
[52] U.S. Cl. ............................................. 128/661.03
[58] Field of Search .................. 128/660.01, 660.03, 128/660.06, 661.03

[56] References Cited

U.S. PATENT DOCUMENTS

| 4,774,959 | 10/1988 | Palmer et al. | 128/660.06 |
| 4,913,157 | 4/1990 | Pratt, Jr. et al. | 128/661.03 |
| 5,197,475 | 3/1993 | Antich et al. | 128/660.01 |
| 5,433,203 | 7/1995 | Kimura et al. | 128/660.06 |
| 5,564,423 | 10/1996 | Mele et al. | 128/661.03 X |
| 5,603,325 | 2/1997 | Mazess et al. | 128/660.06 |

*Primary Examiner*—Francis Jaworski
*Attorney, Agent, or Firm*—Oblon, Spivak, McClelland, Maier & Neustadt, P.C.

[57] ABSTRACT

The osteoporosis diagnosing apparatus of the invention radiates repeatedly an ultrasonic impulse Ai toward the bone Mb of an examinee and receives an echo Ae from the bone Mb. The received signal is converted into a digital echo signal through an A/D converter (8), and the echo level is detected by a CPU (11). The CPU (11) extracts maximum echo level from among the echo levels detected in a given period of measurement to thereby calculate a bone acoustic impedance Zb based on the extracted maximum echo level, and then calculate the bone density of the examinee based on the calculated acoustic impedance Zb. As the impedance Zb is expressed in the square root of the product of modulus of elasticity and density of a bone, decreased in both the modulus of elasticity and the density synergistically affect the impedance to remarkably decrease the same. Thus the bone acoustic impedance serves as a good index in judging the bone density

44 Claims, 9 Drawing Sheets

— WAVEFRONT OF BONE ECHO Ae (CREST)
------ WAVEFRONT OF BONE ECHO Ae (HOLLOW)
— WAVEFRONT OF RADIATED ULTRASONIC IMPULSE Ai (CREST)
--- WAVEFRONT OF RADIATED ULTRASONIC IMPULSE Ai (HOLLOW)

— WAVEFRONT OF BONE ECHO Ae (CREST)
------ WAVEFRONT OF BONE ECHO Ae (HOLLOW)
— WAVEFRONT OF RADIATED ULTRASONIC IMPULSE Ai (CREST)
--- WAVEFRONT OF RADIATED ULTRASONIC IMPULSE Ai (HOLLOW)

OSTEOPOROSIS DIAGNOSING APPARATUS AND METHOD

TECHNICAL FIELD

This invention relates to a reflection type ultrasonic osteoporosis diagnosing apparatus and method which diagnoses osteoporosis by radiating ultrasonic impulses towards a certain bone (cortical bone) of an examinee and determining echo levels from the surface of the bone;

BACKGROUND ART

With the emergence of an ageing society in recent years the bone disease termed osteoporosis has been becoming a problem. In this disease the calcium is withdrawn from the bones leaving them friable and prone to fracture at the slightest shock. Physical diagnosis is performed mainly by determining the density of bone precisely by means of diagnostic apparatus employing X-rays, typified by DXA apparatus; however, physical diagnosis by means of X-rays is beset by various problems such as the fact that the apparatus is large, and its use is restricted by the need to prevent damage due to radiation exposure.

Accordingly, diagnostic apparatus employing ultrasound have started to become popular as simple apparatus which do not cause such problems. In diagnostic apparatus employing ultrasound the speed and attenuation of ultrasound waves propagated inside the bony tissues are measured and used to estimate the density and elastic modulus (elastic strength) of the bone, and if a low estimated value is obtained it can be deduced that this is because of withdrawal of calcium from the bone, and hence osteoporosis is diagnosed.

For example, in the diagnostic apparatus recorded in Japanese Unexamined Patent 2-104337 and U.S. patent application Ser. No. 193,295 the speed of sound in bony tissue is measured by radiating ultrasonic pulses towards the bony tissue of an examinee which is the measurement site from an ultrasound transducer on one side and receiving the ultrasonic pulses transmitted by the bone tissue at an ultrasound transducer on the other side, and progress in osteoporosis is diagnosed when the speed of sound inside the bony tissue is slow. This is because this diagnostic apparatus acts on the premise that in experience the speed of sound in bony tissue is proportional to bone density.

However, the theoretical basis for linking bone density and the speed of sound is not established: strictly speaking the speed of sound in bony tissue is given by the square root of "the elastic modulus of the bone/bone density" and is not proportional to bone density. Moreover, because the elastic modulus of bone rises as bone density increases so that the modulus of elasticity of bone and bone density contribute to the speed of sound in such a way that they cancel one another out, the speed of sound in bony tissue cannot respond sensitively to an increase in bone density, and the coefficient of correlation between the speed of sound in bony tissue and bone density is decidedly not high. The theoretical basis for a link between bone density and attenuation of ultrasound waves is also not established.

Therefore it is unreasonable to expect highly reliable diagnoses from prior diagnostic apparatus which estimate bone density and the elastic modulus of bone from the results of determination of attenuation of ultrasound waves and the speed of sound in bony tissue.

This invention is a response to the situation above, and its purpose is to offer a reflection type ultrasonic osteoporosis diagnosing apparatus and method which, despite being simple and offering no risk of radiation exposure, can estimate bone density or the elastic modulus of bone more accurately (sensitively) than this sort of prior device and method, and can perform highly reliable diagnoses.

DISCLOSURE OF THE INVENTION

The osteoporosis diagnosing device of this invention diagnoses osteoporosis by setting an ultrasonic transducer against a certain skin surface of an examinee and repeatedly radiating ultrasonic impulses towards bone under the above skin while changing the direction of the emitting and receiving surface of the ultrasonic wave transducer within a certain range of solid angle which includes the line normal to the bone surface above, and for every pulse receiving by means of the above ultrasonic transducer the echo returned from the bone surface, and converting the received signal into a digital echo signal by means of an analogue/digital converter, and performing digital signal processing using the digital echo signals obtained by conversion.

Therefore, according to a 1st aspect of the osteoporosis diagnosing apparatus of this invention an osteoporosis diagnosing apparatus is offered which is provided with an echo level detecting means which detects the echo level from the digital echo signal input above, and a maximum echo level extraction device which extracts the maximum echo level from among a detected plurality of echo levels above, and a decision means which makes a decision as to osteoporosis based on the maximum echo level extracted above, and an output means which outputs the results of the decision of the decision means.

In the 1st aspect of this osteoporosis diagnosing apparatus, there is preferably an additional reflection coefficient calculating means which calculates the ultrasonic reflection coefficient of the bone relative to soft tissue of the examinee based on the extracted maximum echo level above, or an acoustic impedance calculating means which calculates the acoustic impedance of the bone of the examinee. With these decision means these can become able to make a decision on osteoporosis based on the above ultrasonic reflection coefficient or acoustic impedance of bone.

The reason is that the maximum echo level is a monotonically increasing function of the ultrasonic reflection coefficient, and the ultrasonic reflection coefficient is an monotonically increasing function of the acoustic impedance of bone, so that if any of the three increases (or decreases) the other two will also show an accompanying increase (or decrease). The acoustic impedance of bone can be expressed as the square root of (elastic modulus x density) of bone.

Consequently, with the constitution of this invention the acoustic impedance of bone (maximum echo level, ultrasonic reflection coefficient) receive the synergistic effects of a rise in elastic modulus accompanying an increase in density; and therefore it responds more sensitively than the speed of sound with a marked increase. On the other hand, acoustic impedance is also affected synergistically by a decrease in density and a lowering of elastic modulus; and responds more sensitively than the speed of sound with a marked decrease. Consequently the acoustic impedance of bone is a good indicator for deciding bone density.

In calculating the ultrasonic reflection coefficient or the acoustic impedance of bone more accurate estimates can be obtained if it is also possible to take into account degree of attenuation in ultrasound waves during the round trip in soft tissues of the examinee, and hence this is preferred.

In addition, according to a 2nd aspect of an osteoporosis diagnosing device of this invention, an osteoporosis diagnosing apparatus is offered which diagnoses osteoporosis by setting against a certain skin surface of an examinee the ultrasonic retarding spacer of an ultrasonic transducer fitted with an ultrasonic retarding spacer in order to eliminate the residual effect of the emitted signal at the emitting and receiving surface of the ultrasonic oscillator, and repeatedly radiating ultrasonic impulses towards bone under the skin above while changing the direction of the emitting and receiving surface of the ultrasonic oscillator within a certain range of solid angle which includes the line normal to the bone surface above, and for every pulse receiving a 1st echo returned from the skin surface above, and then the 2nd echo returned from the bone surface above, at the emitting and receiving surface of the ultrasound wave oscillator above, and converting the received signal into 1st and 2nd digital echo signals by means of an analogue/digital converter, and performing digital signal processing using the 1st and 2nd digital echo signals obtained by conversion.

In addition, the method of diagnosing osteoporosis of this invention diagnoses osteoporosis by setting an ultrasonic transducer against a certain skin surface of an examinee and repeatedly radiating ultrasonic impulses towards bone under the skin above, while changing the direction of the emitting and receiving surface of the ultrasonic transducer within a certain range of solid angle which includes the line normal to the bone surface above, and for every pulse receiving the echo returned from the bone surface by means of the ultrasonic transducer above and determining the echo level, and further extracting the maximum echo level from among a determined plurality of echo levels above, and estimating bone density and the elastic modulus of the bone based on the extracted maximum echo level. The wave of maximum echo level is received when the line normal to the bone and the line normal to the emitting and receiving surface of the ultrasonic transducer coincide, and at this time vertical reflection from the bone is also vertically incident to the emitting and receiving surface. When the line normal to the bone and the line normal to the emitting and receiving surface coincide the echo level is stable irrespective of greater or lesser deviation in the direction of the emitting and receiving surface, so that measurement data with good reproducibility are obtained.

BEST MODE FOR CARRYING OUT THE INVENTION

The best mode for carrying out this invention will be explained below with reference to the drawings. The explanation is in concrete terms using embodiments.

The 1st Embodiment

Figure 1:
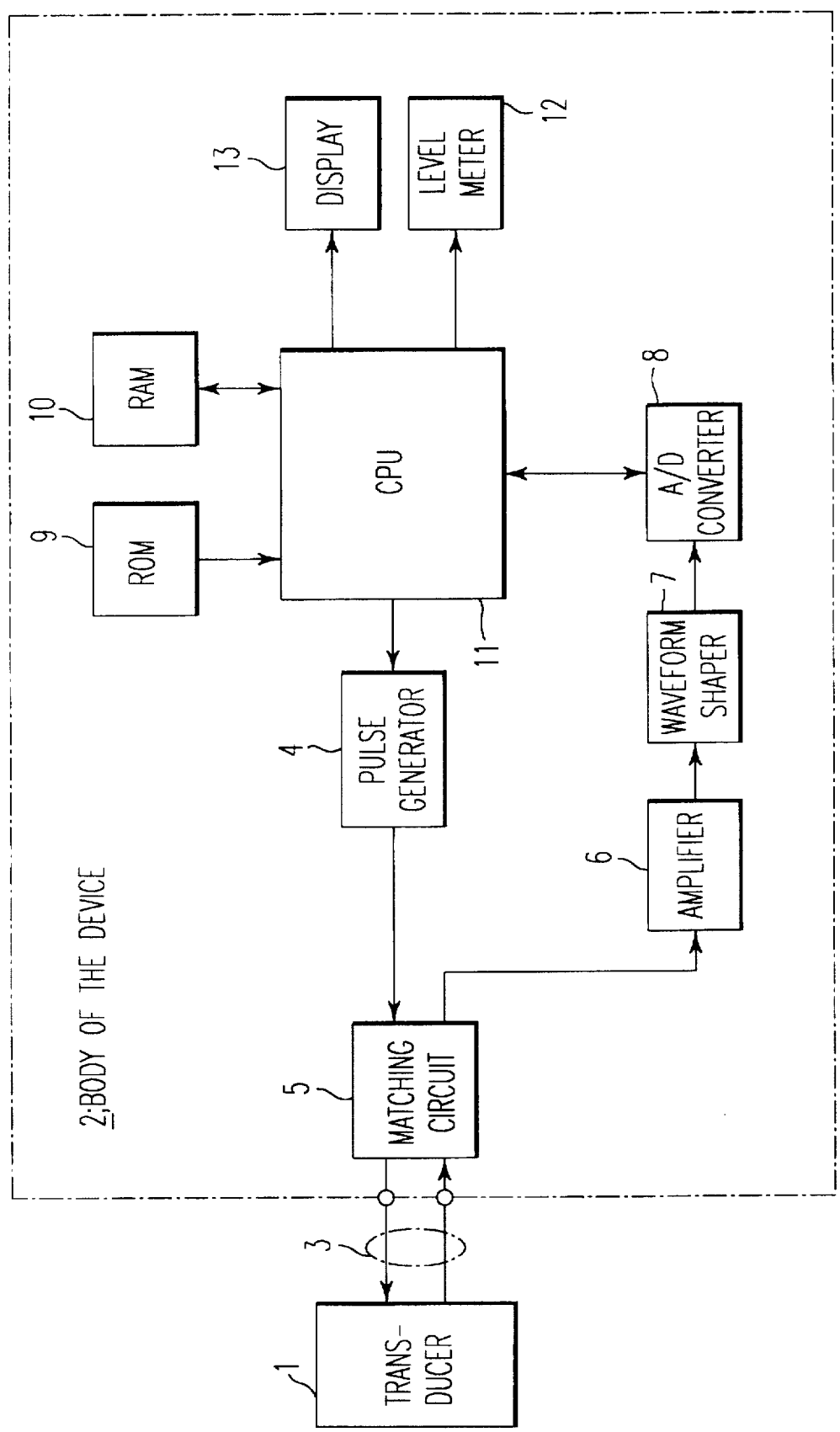
FIG. 1 is a block diagram showing the electrical components of an osteoporosis diagnosing apparatus which is a 1st embodiment of this invention.
Figure 2A:
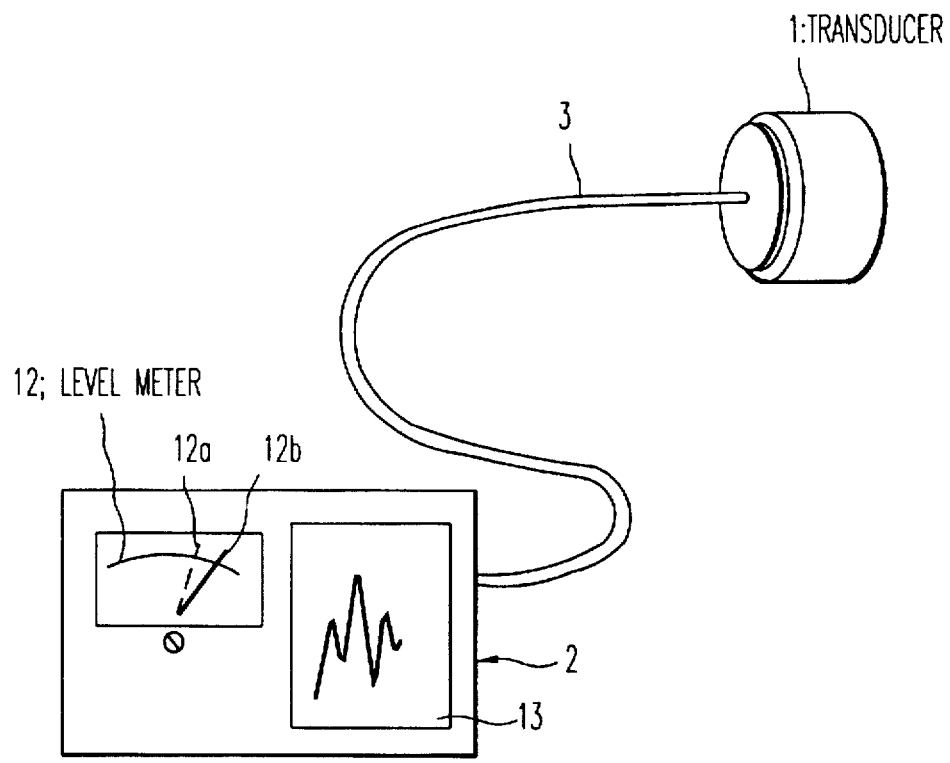
FIG. 2 is an outer view of the same apparatus.
Figure 3:
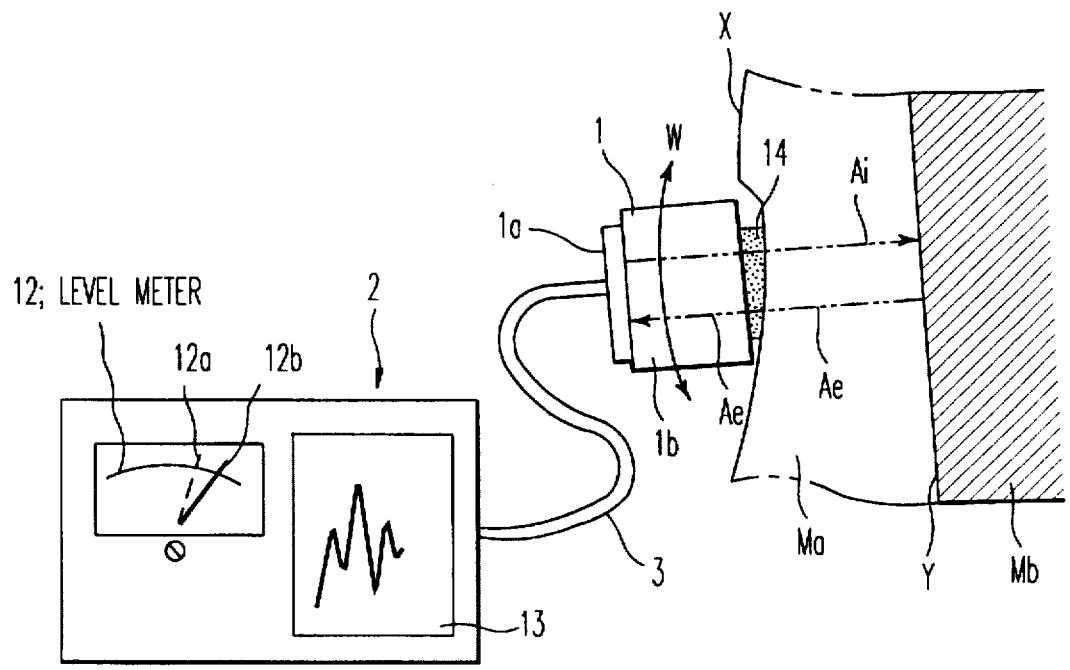
FIG. 3 is a schematic drawing showing the mode of employment of the same apparatus.
Figure 4:
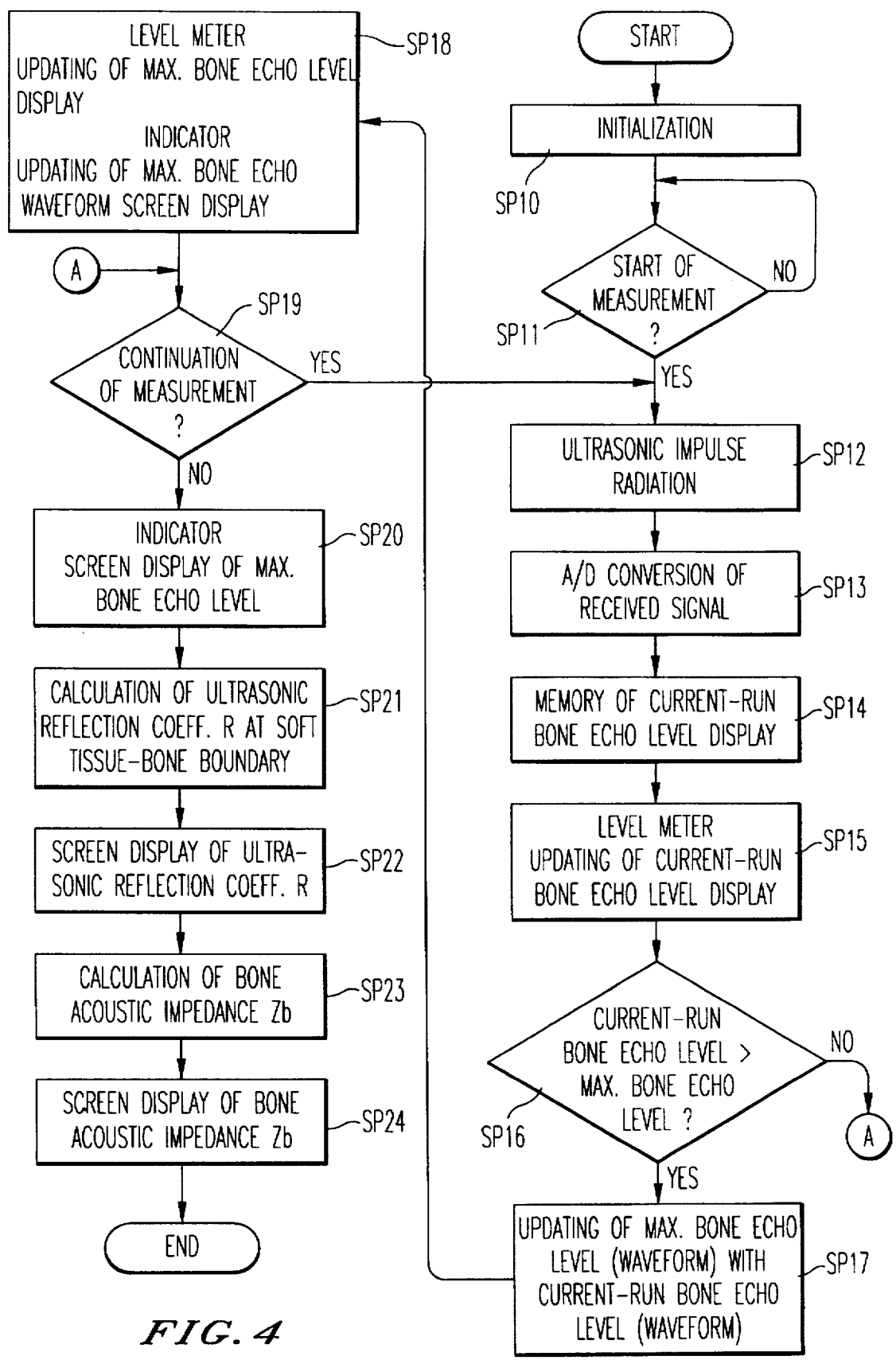
FIG. 4 is a flow chart showing the operating and processing routines of the same device.
Figure 5A:
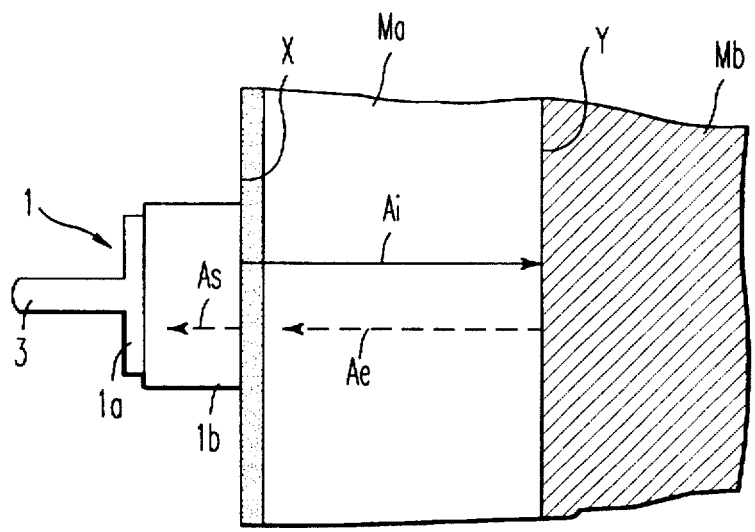
FIG. 5 is a drawing used to explain the action of the same device.
Figure 5B:
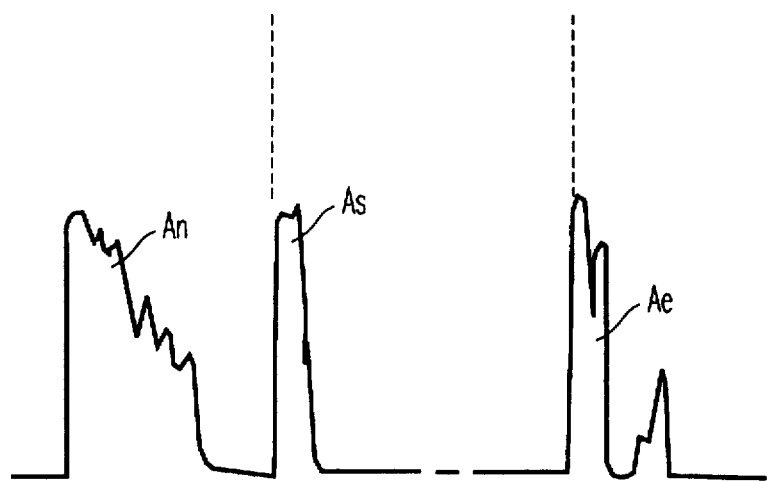
Figure 6A:
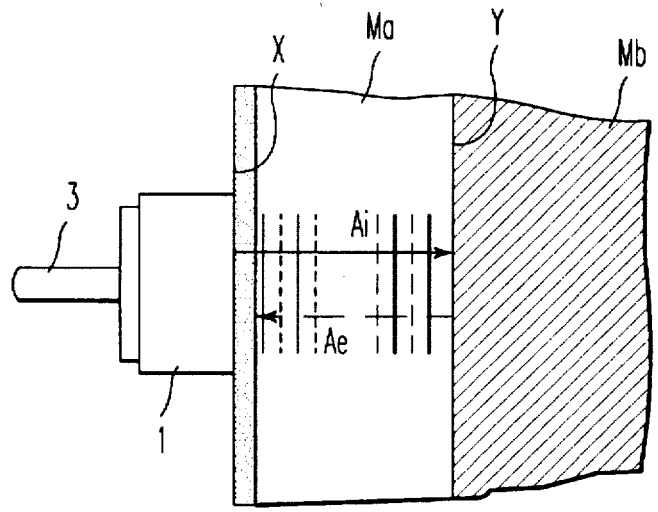
FIG. 6 is also a drawing used in explaining the action of the same device.
Figure 6B:
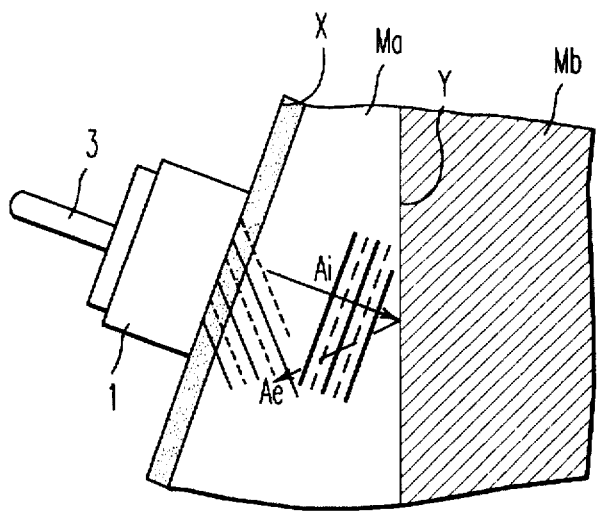

FIG. 1 is a block diagram showing the electrical components of an osteoporosis diagnosing apparatus which is a 1st embodiment of this invention; FIG. 2 is an outer view of the same device; FIG. 3 is a schematic drawing showing the mode of employment of the same apparatus; FIG. 4 is a flow chart showing the operating and processing routines of the same device; FIG. 5 is a drawing used to explain the action of the same device; FIG. 6 is also a drawing used to explain the action of the same device.

As FIG. 1 to FIG. 3 show, the osteoporosis diagnosing apparatus of this example essentially comprises an ultrasonic transducer 1 (called simply a transducer hereafter), which when a half-wave impulse electrical signal is input in a certain cycle, responds by radiating an ultrasonic impulse Ai towards a certain bone Mb of an examinee at a measurement site, and receives the echo (called bone echo hereafter) Ae returned from the surface Y of the bone (cortical bone) Mb and converts it to a received signal (electrical signal), and the body of the apparatus 2 which feeds half-wave impulse electrical signals to the transducer 1, and performs the diagnosis of osteoporosis by extracting bone echo levels which are the amplitudes of the reflected waves from the bone Mb by processing the received signal above output from the transducer 1, and a cable 3 which connects the transducer 1 and the body of the apparatus 2.

The main component of the transducer 1 above is an ultrasonic oscillator 1a having electrode layers on both sides of a thick disk-shaped oscillating type piezoelectric element of lead zirconate titanate (PZT), etc., and an ultrasonic retarding spacer 1b is affixed to one electrode surface of this ultrasound oscillator 1a (the surface emitting and receiving the ultrasonic impulses Ai) in order to eliminate the residual effects of the emitted signal. When the residual emitted signal has no effect on the received wave of the bone echo Ae the ultrasonic retarding spacer 1b can be omitted. In order to perform highly precise determinations here, it is desirable that unimpeded ultrasonic impulses Ai which can be regarded as plane waves from the emitting and receiving surface of the transducer 1 can be radiated towards the bone Mb, and that unimpeded bone echoes Ae which can be regarded as plane waves are returned. Therefore, a transducer 1 in which the emitting and receiving surface is made as wide as possible by constituting it with disk shaped piezoelectric elements which have a comparatively large radius is ideal. From the same point of view, a bone Mb with a large radius of curvature which can be regarded as a flat surface, and is close to the surface of the skin, such as the heel, the upper part of the knee cap or the shin is preferably made the measurement site.

The body of the apparatus 2 above is constituted by a pulse generator 4, a matching circuit 5, an amplifier 6, a waveform shaper 7, an A/D converter 8, a ROM 9, a RAM 10, a CPU (central processing unit) 11, a level meter 12 and a display 13. The pulse generator 4 is connected to the transducer 1 via the cable 3, and produces half-wave impulse electrical signals of a central frequency of almost 2.5 MHz repeating in a certain cycle (e.g. 100 msec), which are sent to the transducer 1. The matching circuit 5 matches impulses between the transducer 1 and the body of the apparatus 2 connected via the cable 3 so that signals can be sent and received with the maximum energy efficiency. Consequently, when the ultrasonic oscillator 1a of the transducer 1 receives a bone echo Ae a received signal is output from the transducer 1, and is input to the amplifier 6 via the matching circuit 5 without any loss of energy. The amplifier 6 amplifies received signals input through the matching circuit 5 to a certain amplitude, and then inputs them to the waveform shaper 7. The waveform shaper 7 comprises a band filter constituted by an LC, and filters received signals amplified by the amplifier 6, shaping the waveform into a linear shape from which the noise component should have been removed, and then inputs them to the A/D converter 8. The A/D converter 8 is provided with a sample holding circuit and a sampling memory (SRAM), etc., and following a sampling start demand from the CPU 11 it samples input signals (waveform shaped analogue received signals) output by the waveform shaper 7 at a certain frequency (e.g. 12 MHz), and converts them sequentially to digital echo signals (called bone echo signals hereafter), and after temporarily storing the resulting bone echo signals in its own sampling memory it issues them to the CPU 11.

The ROM 9 houses the processing program, other than the operating system (OS), which the CPU 11 executes in order to diagnose osteoporosis. This processing program describes a routine for taking up a bone echo signal from the A/D converter 8 for every pulse and every echo and detecting the bone echo level, a routine for extracting the maximum bone echo level from among many echo bone levels thus detected, a routine for calculating the ultrasonic reflection coefficient R of the bone Mb of the examinee relative to soft tissue Ma, and a routine for calculating the acoustic impedance Zb of the bone Mb of the examinee based on the ultrasonic reflection coefficient R. In this treatment program the acoustic impedance Zb of the bone Mb of the examinee is given by Equation (1).

$$Zb=Za(R+1)/(1-R) \quad (1)$$

Za: The acoustic impedance of soft tissue (already known)

When the surface Y of the bone Mb here is regarded as almost flat, and the ultrasonic impulses Ai radiated from the transducer 1 are also regarded as being plane waves, and moreover the wave front thereof are also regarded as almost parallel with the surface Y of the bone Mb (in other words when the ultrasonic impulses Ai are incident almost vertically at the surface Y of the bone Mb), the ultrasonic reflection coefficient R of the bone Mb of the examinee relative to soft tissue Ma can be represented by Equation (2). In this connection, the bone echo level is greatest when the ultrasonic impulse Ai is almost vertically incident at the surface Y of the bone Mb. Therefore, the maximum echo level extracted by this example, as will be discussed hereafter, is obtained when the ultrasonic impulses Ai are vertically incident at the surface Y of the bone Mb, and hence the ultrasonic reflection coefficient R calculated from the extracted maximum echo level corresponds to the ultrasonic reflection coefficient R given by Equation (2). Equation (1) is obtained by transforming Equation (2).

$$R=(Zb-Za)/(Zb+Za) \quad (2)$$

The RAM 10 has a working area designated as the working area for the CPU 11, and a data area where data are temporarily stored; in the data area there is an echo data memory area which stores the bone echo level detected in the current run (current-run bone echo level) and the maximum bone echo level extracted from the bone echo levels detected up until the current run, and a waveform memory area which stores the bone echo waveform of the wave received in the current run and the waveform of the wave received when the maximum bone echo level was detected (maximum bone echo waveform), and a continuation of measurement flag which stores information on whether or not measurement is continuing, etc.

By executing the processing programs mentioned above which are stored in the ROM 9, using the RAM 10, the CPU 11 controls each component of the apparatus starting with the pulse generator 4 and the A/D converter 8, and for every single wave pulse and echo takes up a bone echo signal from the A/D converter 8, detects the echo level then extracts the maximum echo level from among them, and calculates the ultrasonic reflection coefficient R of the bone Mb of the examinee relative to soft tissue Ma on the basis of the value of the extracted maximum echo level, and performs the diagnosis of osteoporosis by calculating the acoustic impedance Zb of the bone Mb of the examinee based on the calculated ultrasonic reflection coefficient R.

The level meter 12 is controlled by the CPU 11 and displays simultaneously the current-run bone echo level stored in the RAM 10 as the deflection of a liquid crystal needle pattern 12a shown in the broken line in FIG. 2 and FIG. 3, and the maximum echo level detected to date (up to the current run) as the deflection of a liquid crystal needle pattern 12b shown by the solid line in the same drawings. The display 13 comprises a CRT display or liquid crystal display, etc., which is controlled by the CPU 11 and displays on a screen the maximum bone echo level (measured value), the ultrasonic reflection coefficient R (calculated value), the acoustic impedance Zb (calculated value), the current-run bone echo waveform and the maximum bone echo waveform, etc.

Next, the operation of this example will be explained with reference to FIG. 3 to FIG. 6 (primarily the flow of CPU 11 processing when diagnosing osteoporosis).

Firstly, cortical bone of a bone Mb with a large radius of curvature, close to the skin surface, such as the heel, the upper knee cap or the shin bone, etc., is selected as a measurement site. These are preferred because unimpeded bone echoes Ae which can be regarded as plane waves are returned from such bone Mb, and hence precision is higher. The power source is plugged into the apparatus, and the CPU 11 resets each of the components of the apparatus, and initializes counters, resistors and flags (Step SP10 (FIG. 4)); and then the switch for the start of measurement is pushed down (SP11). As FIG. 3 shows, here the operator smears an ultrasonic gel 14 on the surface of soft tissue Ma (skin surface X) covering the bone Mb which is the measurement site in the examinee, sets the transducer 1 against the surface of the skin X via the ultrasonic gel 14 with the emitting and receiving surface towards the bone Mb, and switches the start of measurement switch ON. Once the start of measurement switch has been turned ON, (Step SP11), the CPU 11 writes [1] to the continuation of measurement flag, and after setting up the continuation of measurement flag, this starts diagnostic operation following the processing routines shown in FIG. 4.

The CPU 11 first issues a 1 pulse generation command to the pulse generator 4 (Step SP12). When the pulse generator 4 receives the 1 pulse generation command from the CPU 11, it sends a half-wave impulse electrical signal to the transducer 1. On receiving the half-wave impulse electrical signal fed from the pulse generator 4, the transducer 1 radiates an ultrasonic impulse Ai towards the bone Mb of the examinee (which can be regarded as an unimpeded plane wave over the short distance handled). As shown in FIG. 5, the radiated ultrasonic impulse Ai is partially reflected at the surface of the skin X, and the remainder enters soft tissue Ma from the surface of the skin X and propagates towards the bone Mb. Part is then reflected at the surface of the bone Mb and becomes the bone echo Ae, part is absorbed by the bone Mb, and the remainder is transmitted by the bone Mb. The bone echo Ae passes along the reverse path to the incident ultrasonic wave, and is received again by the ultrasonic oscillator 1a of the transducer 1.

Consequently, after radiating the ultrasonic impulse Ai, the ultrasonic transducer 1 receives first the residual sound of the emitted signal An, then the echo from the surface of the skin (called the surface echo hereafter) As, and then slightly later the bone echo Ae by means of the ultrasonic oscillator 1a, and these are converted to received signals of corresponding ultrasonic waveforms and amplitudes. The received signals that are produced are input via the cable 3 to the body of the apparatus 2 (matching circuit 5), amplified to a desired amplitude by the amplifier 6, and after being shaped to a linear waveform by the waveform shaper 7 they are input to the A/D converter 8.

After the CPU 11 has emitted the 1 pulse generation command to the pulse generator 4 (Step SP12), it times the time for the bone echo Ae to be returned to the emitting and receiving surface of the ultrasonic oscillator 1a of the transducer 1 after the residual sound of the emitted signal has been received by the ultrasonic oscillator 1a of the transducer 1 and then the surface echo As has been received, and issues a start of sampling command to the A/D converter 8 (Step S13). On receiving the start of sampling command from the CPU 11, the A/D converter 8 samples the received signals of each individual echo from the bone Mb which are input from the waveform shaper 7 after shaping the waveform, at a certain frequency (e.g. 12 MHz), converts them to digital signals, and temporarily stores the resulting N sample values (digital signals for single echoes) in its own sampling memory. It subsequently issues the N sample values stored in the sampling memory in sequence to the CPU 11, in accordance with transfer orders from the CPU 11.

The CPU 11 takes up the N sample values in sequence from the A/D converter 8, and after recording in the waveform memory area of the RAM 10 as the current-run bone echo waveform, the current-run bone echo level (current-run bone echo amplitude) is detected by extracting the highest value from among the N sample values, and the result of detection is stored in the echo data memory area of the RAM 10 (Step SP14). The current-run bone echo level stored in the RAM 10 is displayed as the deflection of a liquid crystal needle pattern 12a on the level meter 12 as shown by the broken line in FIG. 3 (Step SP15).

Then the CPU 11 reads out the current-run bone echo level and the maximum bone echo level from the echo data memory area inside the RAM 10, and decides whether or not the value of the current-run bone echo level is larger than the value for maximum bone echo level (Step SP16). Since this is the initial decision the value for the maximum bone echo level is still the initial value [0], and so the CPU 11 decides that the value of the current-run bone echo level is greater than the value of the maximum bone echo level, and the value of the maximum bone echo level stored in the echo data memory area of the RAM 10 is rewritten to the value of the current-run bone echo level, and the maximum bone echo waveform recorded in the waveform memory area of the RAM 10 is rewritten to the current-run bone echo waveform (Step SP17). The updated maximum bone echo waveform is displayed on the screen of the display 13, and the updated maximum bone echo level is displayed as a deflection of a liquid crystal needle pattern 12b on the level meter 12, as shown by the solid line in FIG. 3 (Step SP18).

Then the CPU 11 checks for the continuation of measurement flag in the RAM 10 (Step SP19) and if the continuation of measurement flag is standing (when the content of the continuation of measurement flag is [1]) the CPU 11 decides to continue measurement, and after repeating the procedure for radiating 1 pulse and receiving 1 echo (Steps SP12–SP15), in Step 16 it again reads out the current-run bone echo level and the maximum bone echo level from the echo data memory area in the RAM 10, and decides whether or not the current-run bone echo level value is greater than the maximum echo level value. When the current bone echo level is not larger than the maximum bone echo level the result of this decision is to go directly to Step SP19 without performing an update, and to check for the continuation of measurement flag. The content of the continuation of measurement flag remains [1] as long as the operator does not push the end of measurement switch and the CPU repeats the operations of radiating 1 pulse and receiving 1 echo (Steps SP12–SP15) and extracting the maximum bone echo level (Steps SP16–SP19).

While the CPU 11 repeats the process described above (Steps SP12–SP19), the operator changes the direction of the transducer 1 so that while remaining on the surface of the skin X and directed towards the bone Mb of the site of measurement, the direction of the transducer 1 is changed, sometimes in a circle or spiral as in the precession of coma abberation, and sometimes inclining it from back to front or right to left in a seesaw motion as shown in FIG. 3, changing the angle, to investigate the direction in which the maximum deflection of the liquid crystal needle patterns 12a and 12b of the level meter 12, i.e. the maximum bone echo level, is detected. As FIG. 6(a) shows, the deflections of the liquid crystal needle patterns 12a and 12b of the level meter 12 are largest when the line normal to the bone Mb coincides with the line normal to the emitting and receiving surface of the transducer 1; and therefore, when the wave front of the plane wave ultrasonic impulse Ai is almost parallel to the surface Y of the bone Mb (i.e. when the plane wave ultrasonic impulse Ai is almost vertically incident at the surface Y of the bone Mb).

This is because, as the same drawing (a) shows, then both normal lines coincide the bone echo Ae reflected vertically by the surface Y of the bone Mb returns vertically to the emitting and receiving surface of the transducer 1, and consequently the wave front of the bone echo Ae is aligned almost parallel with emitting and receiving surface of the transducer 1 so that there is the minimum of phase deviation of the bone echo due to a difference in the position at which it received by the emitting and receiving surface, and there is little interference between crests and hollows of received signals, and therefore the bone echo Ae of the maximum bone echo level is received. By contrast, when the two normal lines do not coincide, as the same drawing (b) shows, the wave fronts of the bone echo Ae are unaligned at the emitting and receiving surface, so that interference between crests and hollows diminishes the received signal. For this reason, when the bone echo level peaks as the operator changes the angle of the transducer 1 in the vicinity of the line normal to the bone Mb it can be reckoned that the reflected bone echo Ae has been returned almost vertically to the emitting and receiving surface of the transducer 1 by the surface Y of the bone Mb.

The important thing here is that in the diagnostic apparatus of this invention in order to raise precision it is necessary to extract the vertically reflected bone echo Ae. This is because Equation (1) which leads to the acoustic impedance of the bone, as mentioned above, is the equation which holds for an almost vertically reflected bone echo Ae. However, it is not difficult to extract the perpendicularly reflected echo: the vertically reflected echo can be discovered easily by observing the deflections of the liquid crystal needle patterns 12a and 12b of the level meter 12. In other words, when the non-coincidence of the line normal to the bone Mb and the line normal to the emitting and receiving surface of the transducer 1 is extreme the liquid crystal needle patterns 12a and 12b of the level meter show sensible deflections, so that extreme non-coincidence between the two normal lines can be recognized; on the other hand, when the two normal lines are close to coincidence the bone echo level is stable to deviations in the direction of the emitting and receiving surface of the transducer 1 and the deflections of the liquid crystal needle patterns fall, enabling recognition of coincidence of the two normal lines.

The operator watches the deflections of the liquid crystal needle patterns 12a and 12b of the level meter 12, and when it is judged that the maximum bone echo level has been extracted he/she pushes down the end of measurement switch. Once the end of measurement switch has been pressed down, the CPU 11 writes the content of the continuation of measurement flag to [0] by an interruption process, and the continuation of measurement flag goes down. Once the continuation of measurement flag goes down, the CPU 11 stops the radiation of subsequent pulses (Step SP19). The maximum bone echo level recorded in the echo data memory area of the RAM 10 is then read out, and displayed on the panel of the display 13 (Step SP20).

After this, the CPU 11, calculates the ultrasonic reflection coefficient R of the interface between soft tissue Ma and bone Mb of the examinee from the maximum bone echo level Ve stored in the echo data memory area of the RAM 10, and the total echo level V0 previously stored in ROM by executing the reflection coefficient calculation routine (Step SP21), and displays the calculated value on the panel of the display 13 (Step SP22).

The ultrasonic reflection coefficient R here is derived from the ratio of the total echo level V0 and the maximum bone echo level Ve when the reflection is completely vertical (R=Ve/V0 ); the total echo level can be calculated theoretically, but it is also possible to find it by radiating an ultrasonic impulse towards air and determining the open echo level when the open echo returned from the end face of an ultrasonic retarding spacer (dummy block) 1b of polyethylene bulk, etc., is received by the ultrasonic oscillator 1a. Then, the CPU 11, calculates the acoustic impedance Zb (kg/m$^2$. sec) of the bone Mb by executing the acoustic impedance calculating routine, by substituting into Equation (1) the value for the ultrasonic reflection coefficient R given by the reflection coefficient calculating routine (Step SP23), and displays the result of the calculation on the panel of the display 13 (Step SP24).

With the constitution above, when the line normal to the bone and the line normal to the emitting and receiving surface almost coincide the echo level is stable to greater or lesser deviations in the direction of the emitting and receiving surface (the deflection of the liquid crystal needle patterns 12a and 12b of the level meter falls), and therefore the bone echo level during vertical reflection, i.e. maximum bone echo can be easily extracted, and moreover, measurement data can be obtained with good reproducibility. In addition, the fact that the maximum bone echo level is also shown as a fixed value on the level meter 12 as long as it is not updated, in addition to the current bone echo level, makes it even more easy to investigate the maximum bone echo level. Therefore, the acoustic impedance Zb of the bone Mb can be found with good precision.

The acoustic impedance Zb of the bone Mb is represented by the square root of (elastic modulus×density] of the bone Mb, and hence if bone density increases and elastic modulus also rises it is synergistically affected and responds more sensitively than the speed of sound, with a marked increase. On the other hand if bone density decreases and elastic modulus is also lowered, acoustic impedance is synergistically affected and responds more sensitively than the speed of sound with a marked decrease. Consequently, the acoustic impedance Zb of the bone Mb becomes a good indicator for judging bone density. Therefore, from the value for acoustic impedance of the bone Mb displayed on the display 13 the operator can estimate accurately the situation as far as the progress of osteoporosis is concerned. For example, when the acoustic impedance is considerably smaller than the average value for the age group it is evident that there has been a deterioration in osteoporosis in the bone Mb.

In addition, since only the bone echo level detected in the current run and the maximum bone echo level are stored in the echo data memory area of the RAM 10 and echo levels detected previously are erased unless they are the maximum echo level, a cheap RAM with a small memory capacity can be employed. Of course, a RAM with a large memory capacity can also be used, with all of the bone echo levels detected during the entire measurement period being temporarily stored and the maximum bone echo level being extracted after finishing the measurements from among all of the echo levels recorded in the RAM.

The 2nd Embodiment

A 2nd embodiment of this invention will next be explained.

This 2nd embodiment has almost the same constitution as the 1st embodiment, except for the adoption of an algorithm for calculating the ultrasonic reflection coefficient which is different from the 1st embodiment discussed above.

In the 2nd embodiment the ultrasonic reflection coefficient R of the bone Mb relative to soft tissue Ma is given by Equation (3), when the ultrasonic impulse Ai and the bone echo Ae can be regarded as adequately plane waves and the attenuation of ultrasound waves by soft tissue Ma can be ignored.

$$R = Ve/p \cdot Q \cdot B \cdot Vi \tag{3}$$

p: The sound pressure of the ultrasonic impulse output in an almost vertical direction from the emitting and receiving surface of the transducer 1 when a unit electrical signal (voltage, current, scattering parameter) is applied to the transducer 1

Q: The amplitude of the received signal (electrical signal) output from the transducer when an echo of a unit sound pressure is vertically incident at the emitting and receiving surface of the transducer B: The product of degree of amplification of the amplifier 6 and degree of increase in amplification of the waveform shaper 7

Vi: The amplitude of the electrical signal (voltage, current, scattering parameter) applied to the transducer 1 from the pulse generator 4

Ve: The maximum bone echo level

It should be noted that P, Q, B and Vi are all functions of frequency, and here a component at a central frequency (e.g. 2.5 MHz) is used. As far as P, Q, B and Vi are concerned, the measured values and set values for these are written beforehand into the ROM 9.

Equation (3) is derived as follows. Firstly, when an electrical signal of amplitude Vi is applied to the transducer 1 from the pulse generator 4, an ultrasonic impulse of sound pressure PVi is output from the emitting and receiving surface of the transducer 1 towards the bone Mb. Consequently, a bone echo Ae of sound pressure RPVi is returned vertically to the emitting and receiving surface of the transducer 1. Therefore, the maximum bone echo level Ve is given by Equation (4).

$$Ve = Q \cdot R \cdot P \cdot B \cdot Vi \qquad (4)$$

Rearrangement of this Equation (4) gives Equation (3).

Since the acoustic impedance Zb of the bone Mb is thus also calculated by the CPU 11 from the ultrasonic reflection coefficient R in the 2nd embodiment, almost the same benefits can be obtained as in the 1st embodiment.

The 3rd Embodiment

Figure 7:
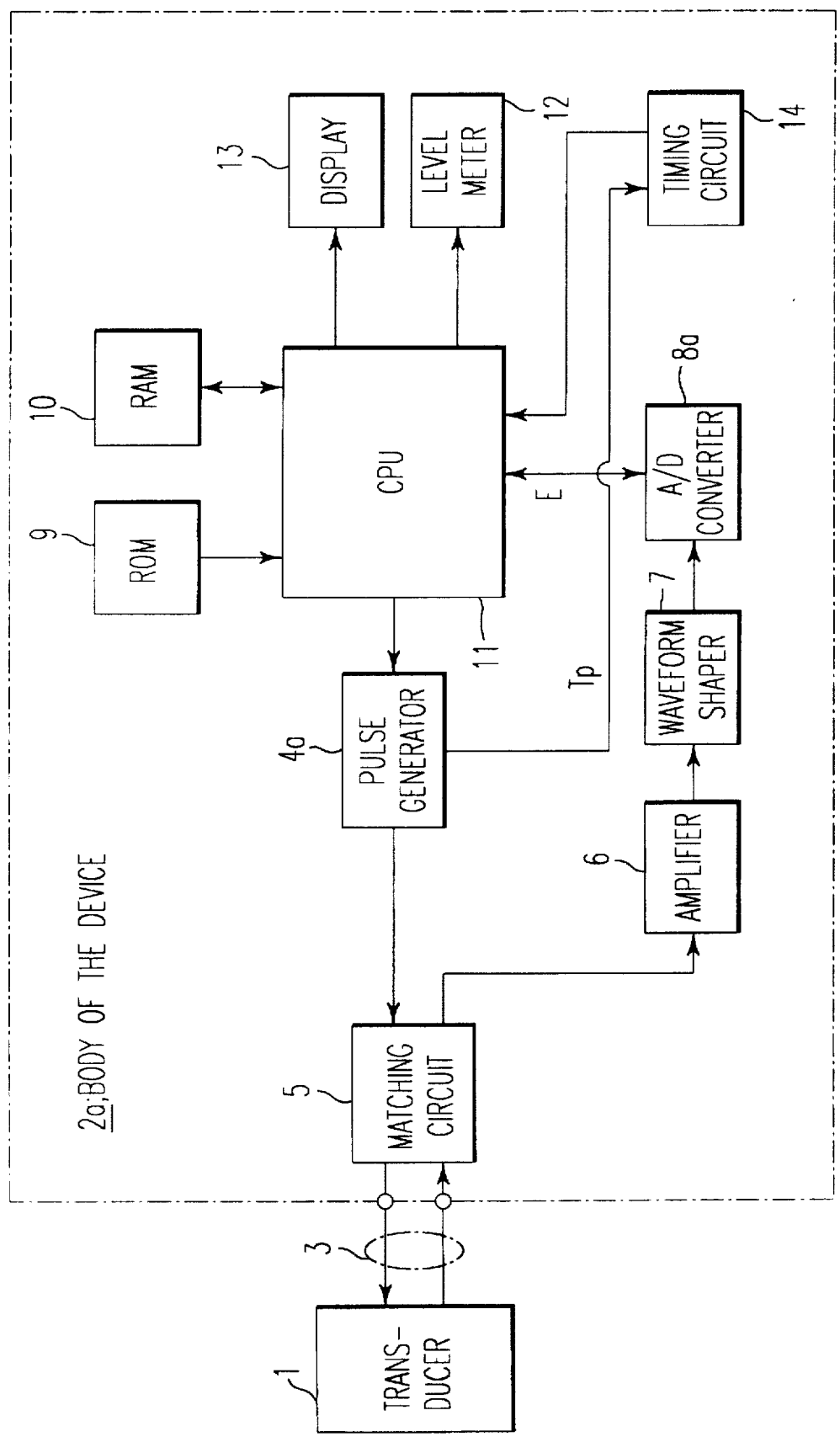
FIG. 7 is a block diagram showing the electrical components of an osteoporosis diagnosing apparatus which is a 3rd embodiment of this invention.
Figure 8:
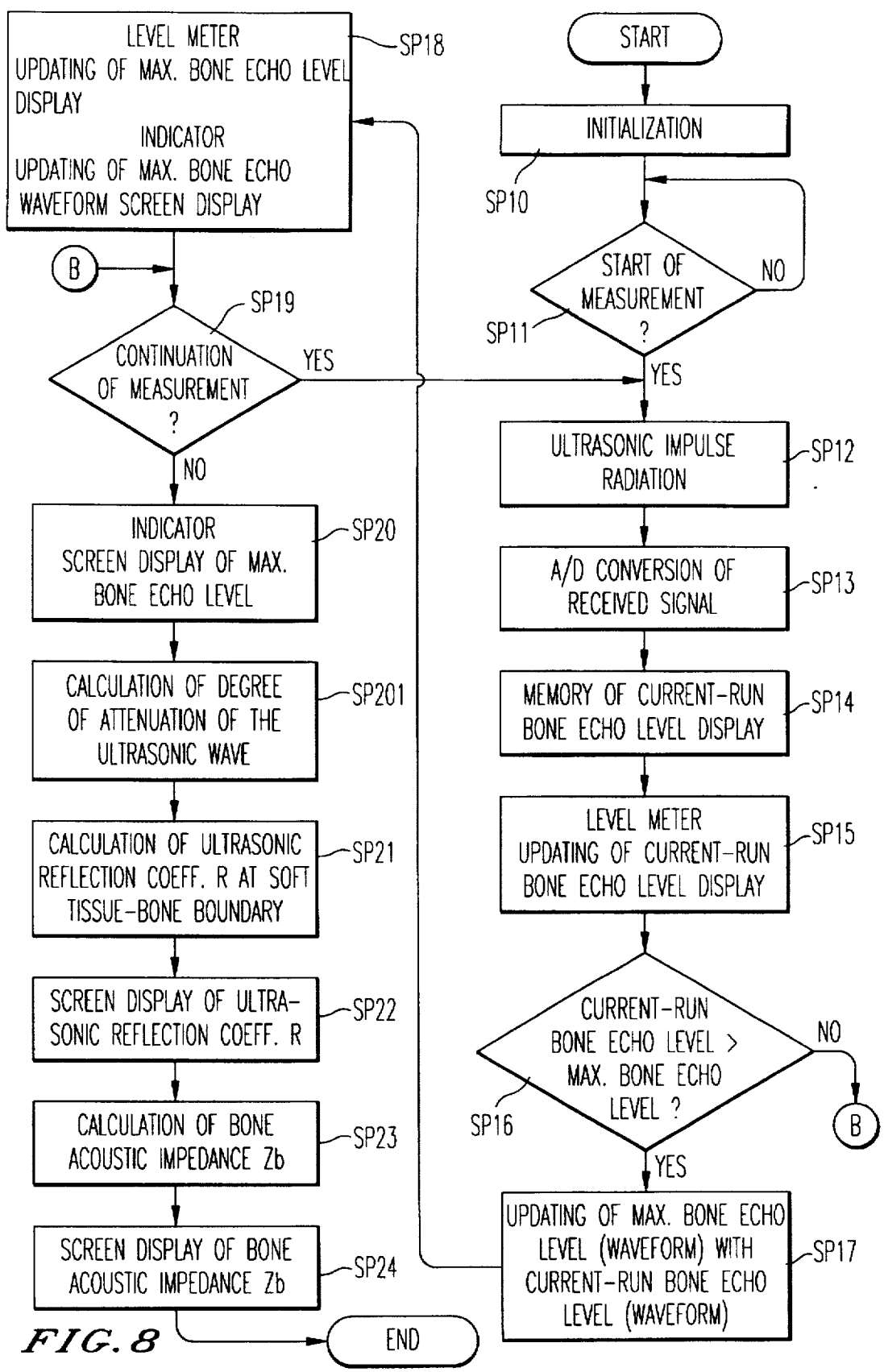
FIG. 8 is a flow chart showing the operating and processing routines of the same device.

FIG. 7 is a block diagram showing the electrical components of an osteoporosis diagnosing apparatus which is a 3rd embodiment of this invention; and FIG. 8 is a flow chart showing the operating and processing routines of the same apparatus.

The big difference between this 3rd embodiment and the 2nd embodiment discussed above is that the acoustic impedance Zb of the bone Mb can be determined with certainty by considering degree of attenuation of ultrasound waves A(T) due to the round trip through soft tissues Ma.

To this end, as FIG. 7 shows, the body of the apparatus 2 of this example has an additional timing circuit 14 which measures the bone echo arrival time T after an ultrasonic impulse Ai has been radiated from the emitting and receiving surface of the transducer 1 for the bone echo Ae to be returned to the emitting and receiving surface. In addition, the processing program of this example includes the description of a routine for calculating the ultrasonic reflection coefficient R of the bone Mb relative to soft tissue Ma of the examinee based on the maximum bone echo level extracted by a similar algorithm to that in the 1st embodiment and the bone echo arrival time T at that time; the CPU 11 calculates the ultrasonic reflection coefficient R by executing the processing program, and a diagnosis of osteoporosis is performed based on the calculated ultrasonic reflection coefficient R. In other points each of the component parts are the same as in FIG. 1, so these component parts are labelled in the same way as component parts shown in FIG. 1, and the explanation thereof is omitted.

In the body of the apparatus 2a of this example, the pulse generator 4a responds to pulse generation commands from the CPU 11 repeated at in a certain cycle, and produces half-wave impulse electrical signals of a central frequency of almost 2.5 MHz in the certain cycle; and as well as sending a signal to the transducer 1 it feeds a start of timing signal Tp to the timing circuit 4 with the same timing as the half-wave impulse signal.

The cycle of the half-wave impulse here is set at a sufficiently longer time than the bone echo arrival time T. The timing circuit 14 is constituted by a clock generator and a counting circuit, not shown in the drawings: timing is started the moment that a start of timing signal Tp fed from the pulse generator 4 is received, and timing is finished when the final signal is received from the A/D converter 8a. The time value is held until it is reset, and the held time value is given to the CPU 11 as the bone echo arrival time in accordance with demands.

The operation of this example (mainly CPU 11 processing flow when diagnosing osteoporosis) will next be explained with reference to FIG. 8. In the processing flow in this example Step SP10 to Step SP20, except for the measurement of the bone echo arrival time T, are almost the same as discussed in the 1st embodiment and so they will only be explained briefly.

In this example, when the CPU 11 reads in a bone echo signal E from the A/D converter 8a in Step SP14 it also reads the bone echo arrival time T from the timing circuit 14 and stores in the echo data memory area of the RAM 10 the current bone echo signal E and the bone arrival time T which have been read in.

After measurement has finished (Step SP19, Step SP20), the CPU 11 first calculates degree of ultrasonic attenuation A(T) in soft tissues Ma of the examinee by executing an ultrasonic attenuation calculation routine, reading out the bone echo arrival time T from the echo data memory area, substituting the read-out value for the bone echo arrival time T(sec) into Equation (5) (Step SP201).

$$A(T) = 10^{\frac{-1.1T}{20 \cdot 0.01/1500}} \qquad (5)$$

Degree of attenuation A(T) here is degree of attenuation in the ultrasonic wave in the round trip within soft tissues Ma: thus, it means degree of attenuation in the ultrasonic wave during its propagation from the surface of the skin X to the surface Y of the bone Mb and reflection by the surface Y of the bone Mb until it is returned again to the surface of the skin Y (the smaller A(T) the greater degree of attenuation). This attenuation A(T) is a function of bone echo arrival time; the equation of the function can be found by experiment or simulation. Ultrasonic waves are attenuated in soft tissues because: 1. the ultrasonic waves employed in this example are probably not completely plane waves but include a spherical wave component, and acoustic energy is diffused by this spherical wave component (ultrasonic diffusion); and 2. acoustic energy is converted into heat energy by friction with soft tissues Ma (ultrasonic absorption). Degree of attenuation caused by ultrasonic diffusion can be found by calculation or experiment from the opening of the transducer 1, the frequency of the ultrasonic waves and the speed of sound in soft tissues Ma. Degree of attenuation due to ultrasonic absorption becomes smaller if the ultrasonic frequency is lowered, and if the frequency is made low enough an absorption constant typical of soft tissue Ma (percentage ultrasonic attenuation per unit length) can be used. In passing, Equation (5) which gives degree of ultrasonic attenuation A(T), is an experimental equation established when the central frequency of the ultrasonic waves employed was set to 2.5 MHz, and the opening of the transducer was set to 15 mm.

The CPU 11 next reads out the maximum bone echo level Ve from the echo data memory area, substitutes this together with degree of attenuation A(T) calculated using Equation (5) into Equation (6), and calculates the ultrasonic reflection coefficient R at the interface between soft tissue Ma and the bone Mb when the ultrasonic wave is vertically incident at the bone Mb from the medium of soft tissue Ma (Step SP21).

$$R = Ve/P \cdot Q \cdot B \cdot Vi \cdot A(T) \qquad (6)$$

The meanings of P, Q, B and Vi are the same as mentioned in Equation (3). Equation (6) is derived as follows.

Firstly when an electrical signal of amplitude Vi is applied to the transducer 1 from the pulse generator 4a, an ultrasonic pulse Ai of sound pressure PVi is injected into soft tissues Ma from the emitting and receiving surface of the transducer 1. The injected ultrasonic pulse Ai attenuated inside soft tissues Ma is reflected vertically by the surface Y of the bone Mb (considering the case when it is vertically incident at the surface Y of the bone Mb), and becomes a bone echo Ae which is returned vertically to the transducer 1.

Consequently, the sound pressure P(e) of the bone echo Ae returned vertically to the emitting and receiving surface of the transducer 1, taking into account degree of attenuation A(T) of the ultrasound wave by the round trip in soft tissues Ma found by Equation (5), is given by Equation (7).

$$p(e)=P \cdot Vi \cdot R \cdot A(T) \tag{7}$$

When the bone echo Ae of sound pressure P(e) is received at the emitting and receiving surface of the transducer 1, the transducer 1 outputs a received signal of amplification Q·P(e), and this received signal is amplified in the amplifier 6 (and the waveform shaper 7) by a degree of amplification B. After digital conversion by the A/D converter 8a, it is taken up by the CPU 11, and detected as a maximum bone echo level $$Ve(=B \cdot Q \cdot p(e)).$$

Consequently, the maximum bone echo level Ve is given by Equation (8).

$$Ve=P \cdot Vi \cdot R \cdot A(T) \cdot B \cdot Q \tag{8}$$

Isolating the ultrasonic reflection coefficient R from Equation (8) gives Equation (6).

To return again to the explanation of the flow chart of FIG. 8, after calculating the ultrasonic reflection coefficient R at the interface between soft tissues Ma and the bone Mb by using Equation (6) (Step SP21), the CPU 11 displays the calculated result on the display 13 (Step SP22).

After this, the CPU 11 calculates the acoustic impedance Zb (N.s/m$^3$) of the bone Mb using Equation (1) (Step SP23), and displays the calculated result on the display 14 (Step SP24).

With the constitution, in addition to the benefits of Embodiment 1 discussed above it is possible to determine the acoustic impedance of the bone Mb with a greater degree of accuracy, since degree of attenuation A(T) of the ultrasonic wave due to the round trip in soft tissues Ma is taken into account.

The 4th Embodiment

Figure 9:
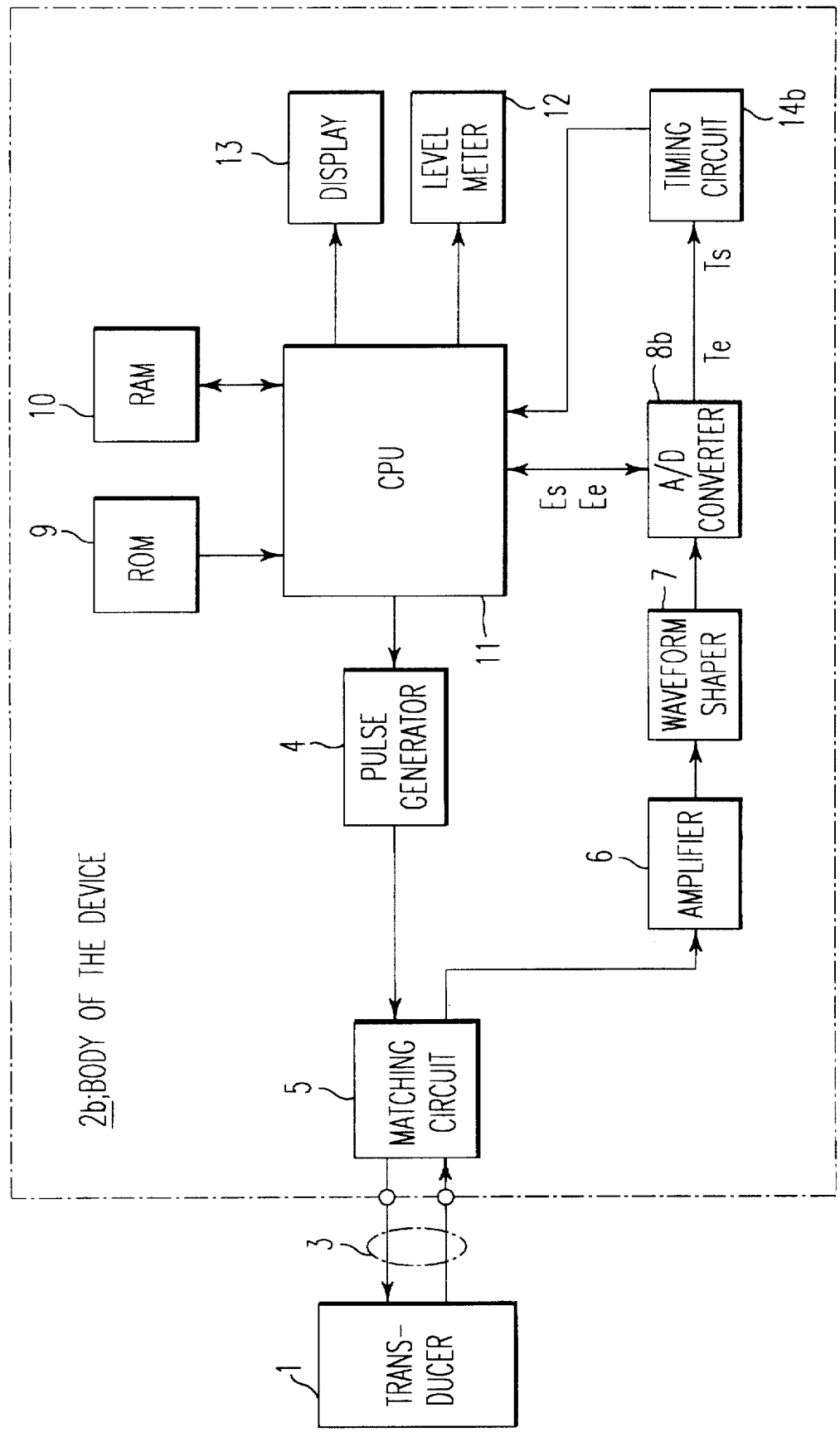
FIG. 9 is a block diagram showing the electrical components of an osteoporosis diagnosing apparatus which is a 4th embodiment of this invention.

FIG. 9 is a block diagram of the electrical components of an osteoporosis diagnosing apparatus which is a 4th embodiment of this invention.

In this 4th embodiment the fact that degree of attenuation A(T) of the ultrasonic wave due to the round trip in soft tissues Ma is considered is the same as in the 3rd Embodiment discussed above; however, it differs from the 3rd embodiment discussed above in that the surface echo As produced by the contact surface X of an ultrasonic retarding spacer 1b with the skin is received, the level thereof (surface echo level) is detected, and degree of attenuation A(T) is calculated based on the detected surface echo level.

Thus, in the body of the apparatus 2b in this example the A/D converter 8b digitalizes in sequence the signal received first after the start of sampling (the received signal relating to the surface echo As) and the signal received next (the received signal relating to the bone echo Ae) as a surface echo signal Es and a bone echo signal Ee, by sampling the input signals output by the waveform shaper 7 (waveform-shaped analogue reception waves) with a set frequency (e.g. 12MHz) following the demand for the start of sampling from the CPU 11, and after storing the surface echo signal Es and bone echo signal Ee obtained by this conversion temporarily in its own sampling memory, they are issued to the CPU 11 in accordance with demands. The A/D converter 8b also produces a surface echo arrival signal Ts when the surface echo As is received, and then produces a bone echo arrival signal Te when the bone echo Ae is received, and gives these to a counting circuit 14b.

The timing circuit 14b is constituted by a clock generator and a counting circuit not shown in the drawings: when a surface echo arrival signal Ts fed from the A/D converter 8b is received, the counting circuit is reset and timing is started; and when the bone echo arrival signal Te is received the counting circuit is ended. The time value is held until it is reset, and the time value held is given to the CPU 11 as the bone echo arrival time T in accordance with demands. The bone echo arrival time T here means the delay between the arrival of the bone echo Ae and a base time (the time of arrival of the surface echo As), and the value obtained by multiplying the bone echo arrival time T by the speed of sound in soft tissues Ma corresponds to twice the thickness of soft tissues: i.e. the distance of the round trip of the ultrasonic wave in soft tissues.

The processing program of this example comprises a processing routine almost the same as that described in the 1st embodiment, but the ultrasonic reflection coefficient R is given by Equation (9).

$$R=[(Za+Zc) \cdot (Za-Zc) \cdot Ve]/[4Za \cdot Zc \cdot A(T) \cdot Vs] \tag{9}$$

Zc: The acoustic impedance of the ultrasonic retarding spacer 1b (measured value or calculated value already known)

Za: The acoustic impedance of soft tissues Ma (measured value or calculated value already known)

Ve: The maximum echo level

Vs: The surface echo level when the maximum echo level is received

T: The bone echo arrival time when the maximum echo level is received

A(T): Degree of ultrasonic attenuation when the maximum echo level is received.

Equation (9) is derived as follows.

Firstly, when a half-wave impulse electrical signal (amplitude Vi) is sent to the transducer 1 from the pulse generator 4 the transducer 1 radiates an ultrasonic impulse Ai towards the bone Mb of the examinee from the emitting and receiving surface of the ultrasonic oscillator 1a. If the sound pressure of the ultrasonic impulse Ai output from the transducer at the end surface of the ultrasonic retarding spacer 1b is P when a unit electrical signal (voltage, current, scattering parameter, etc.) is applied to the transducer, the ultrasonic impulse Ai reaches the end surface of ultrasonic retarding spacer 1b with a sound pressure of PVi; here the majority enters soft tissues Ma from the surface of the skin X, but a part becomes surface echo As, and is received again by the transducer 1 along the reverse path.

The sound pressure P(s) of the surface echo As is given by Equation (10).

$$P(s)=D \cdot P \cdot Vi \tag{10}$$

where $$D=(Z_a-Z_c)/(Z_a+Z_c)$$

D: The ultrasonic reflection coefficient at the interface of the ultrasonic retarding spacer $1b$ and soft tissue Ma when the ultrasonic wave is vertically incident to soft tissue Ma from the ultrasonic retarding spacer $1b$ Now, if the amplitude of the received signal (electrical signal) output from the transducer 1 is Q when an echo of a unit incident sound pressure is incident vertically at the end surface of the ultrasonic retarding spacer $1b$, the transducer 1 outputs a received signal of amplitude Q.P(s) when the surface echo As of the sound pressure P(s) is received at the ultrasound oscillator $1a$ of the transducer 1. This received signal is amplified by the amplifier 6 and the waveform shaper 7, and is digitalized by the A/D converter $8b$ as a surface echo signal Es. Consequently, if the product of the amplitude amplification of the amplifier 6 and the amplitude amplification of the waveform shaper 7 is B, the surface echo level Es is given by Equation (11).

$$E_s=[(Z_a-Z_c)/(Z_a+Z_c)] \cdot B \cdot Q \cdot P \cdot V_i \quad (11)$$

On the other hand, the ultrasonic impulse Ai of sound pressure PVi is injected into soft tissues Ma from the end surface of the ultrasonic retarding spacer $1b$ (skin surface Y) with a sound pressure of PVi.T12. T12 here is the percentage transmittance of ultrasonic sound pressure vertically incident from the medium of the ultrasonic retarding spacer $1b$ to the medium of soft tissue Ma. When the ultrasonic impulse Ai of sound pressure PVi.T12 injected into soft tissues Ma is vertically incident at the bone surface Y, it forms a bone echo Ae which is vertically reflected at the bone surface Y and returned to the transducer 1. The sound pressure F(e) of the bone echo Ae returned vertically to the emitting and receiving surface of the ultrasonic oscillator $1a$, considering degree of ultrasonic attenuation A(T) due to the round trip in soft tissues Ma, is given by Equation (12). It should be noted in passing that the component reflected when the ultrasonic wave is incident on the ultrasonic retarding spacer $1b$ from the medium of soft tissue Ma, and the component of attenuation inside the ultrasonic retarding spacer $1b$, are ignored.

$$P(e)=P \cdot V_i \cdot T_{12} \cdot T_{21} \cdot R \cdot A(T)$$

where

T21: The percentage transmittance of the ultrasound wave incident vertically from the medium of soft tissue Ma to the medium of the ultrasonic retarding spacer $1b$ When the bone echo Ae of sound pressure P(e) is received vertically at the ultrasonic oscillator $1a$ of the transducer 1, the transducer 1 outputs a received signal of amplitude Q.P(e). This reception signal is amplified by the amplifier 6 (and the waveform shaper 7) by a degree of amplification B, and digitalized by the A/D converter as the maximum bone echo signal.

Consequently, the maximum bone echo level Ve is given by Equation (13).

$$V_e=P \cdot V_i \cdot T_{12} \cdot T_{21} \cdot R \cdot A(T) \cdot B \cdot Q \quad (13)$$

The transmittance T12 of sound pressure from the ultrasonic spacer $1b$ to soft tissue Ma here is given by Equation (14).

$$T_{12}=2Z_c/(Z_a+Z_c) \quad (14)$$

Similarly, the transmittance T21 of sound pressure from soft tissue Ma to the ultrasonic retarding spacer $1b$ is given by Equation (15).

$$T_{21}=2Z_a/(Z_a+Z_c) \quad (15)$$

Rearranging Equation (13) using Equations (14) and (15), the maximum bone echo level is given by Equation (16).

$$V_e=P \cdot V_i \cdot R \cdot A(T) \cdot B \cdot Q \cdot 4Z_a \cdot Z_c/(Z_a+Z_c)^2 \quad (16)$$

On substituting Equation (16) into Equation (11), Equation (17) is obtained.

$$V_e=R \cdot A(T) \cdot V_s \cdot 4Z_a \cdot Z_c/[(Z_a+Z_c) \cdot (Z_a-Z_c)] \quad (17)$$

Vs in Equation (17) here is the surface echo level when the maximun echo level Ve is received; Equation (17) can be rearranged to give Equation (19) above, which gives the ultrasonic reflection coefficient R in this example.

In this constitution the CPU 11, by executing the processing program above stored in the ROM 9, using the RAM 10, takes up the surface echo signal Es and bone echo signal Ee from the A/D converter $8b$ for each pulse and echo and detects the surface echo level and the bone echo level by following an algorithm almost the same as in the 1st embodiment, then extracts the maximum bone echo level Ve from among them, calculates the ultrasonic reflection coefficient R given by Equation (9) based on the extracted maximum bone echo level Ve, the surface echo level Vs at this time and the bone echo arrival time T at this time, calculates the acoustic impedance of the bone of the examinee based on the ultrasonic reflection coefficient R, and makes a diagnosis as to osteoporosis using the calculated acoustic impedance of the bone as an index.

The constitution above can also give almost the same benefits mentioned in the 3rd embodiment.

The 5th embodiment

Degree of attenuation A(T) of the ultrasonic wave due to the round trip in soft tissue Ma is also considered in this 5th embodiment. The hardware components of this example are almost the same as those if the 4th embodiment (FIG. 9), but software components, i.e. the algorithms for calculating the ultrasonic reflection coefficient and the acoustic impedance of the bone Mb are different from the 4th embodiment mentioned above.

Thus, in this embodiment the ultrasonic reflection coefficient R at soft tissue Ma/bone Mb interface is given by Equation (18).

$$R=h/[(1+s) \cdot (1-s) \cdot A(T)] \quad (18)$$

where $$h=V_e/p \cdot Q \cdot B \cdot V_i$$

$$s=V_s/P \cdot Q \cdot B \cdot V_i$$

Where the meanings of P, Q, B and Vi are the same as mentioned in Equation (3). The acoustic impedance Za of soft tissue Ma is given by Equation (19), rearranging Equation (11).

$$Z_a=(1+s)/(1-s) \cdot Z_c \quad (19)$$

where $$s=V_s/P \cdot Q \cdot B \cdot V_i$$

Equation (18) is derived from Equation (19) and Equation (16).

17

Similarly, the acoustic impedance Zb of the bone Mb is given by Equation (20).

$$Zb=Zc\cdot(1+s)/(1-s)\cdot(1+R)/(1-R) \qquad (20)$$

where $$s=Vs/P\cdot Q\cdot B\cdot Vi$$

The constitution above can also give almost the same benefits mentioned in the 4th embodiment.

The 6th embodiment

Figure 10:
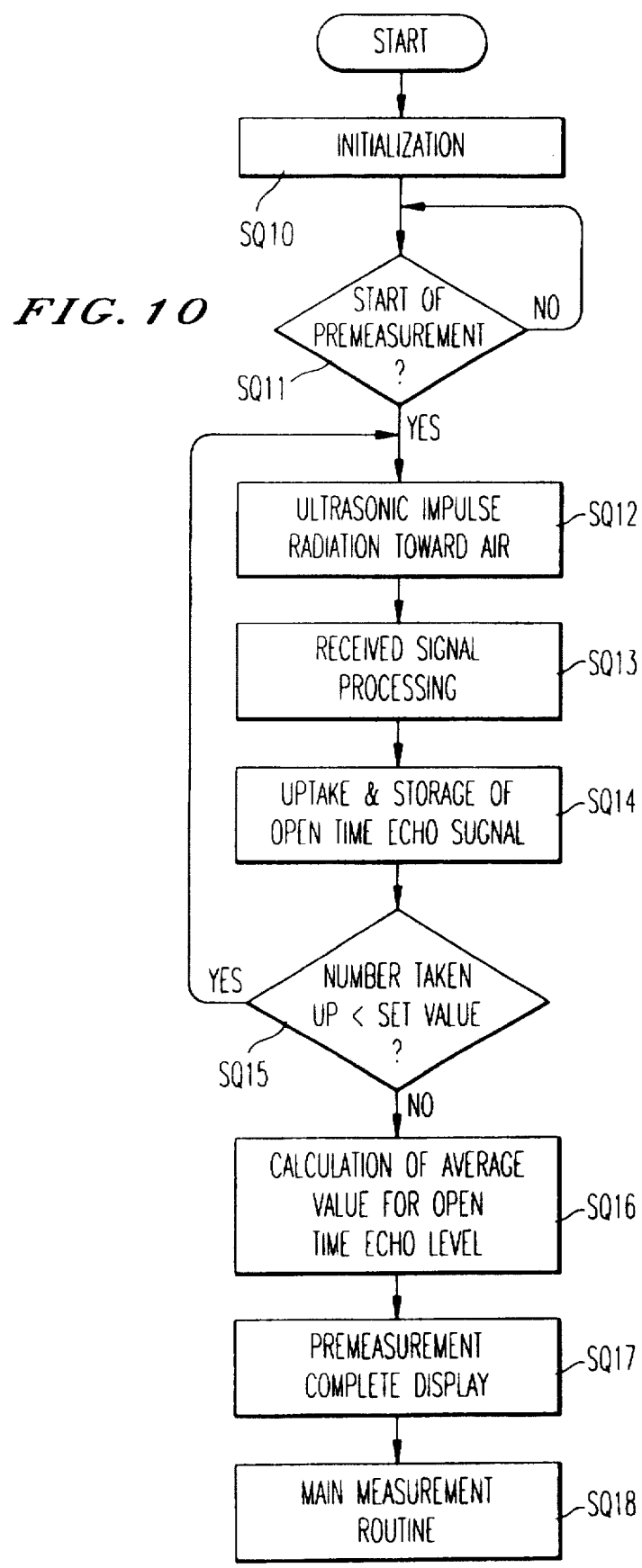
FIG. 10 is a flow chart showing the operating and processing routine of an osteoporosis diagnosing apparatus which is a 6th embodiment of this invention.

FIG. 10 is a flow chart showing the operating and processing routines of an apparatus for diagnosing osteoporosis which is a 6th embodiment of this invention.

This 6th embodiment has in common with the 4th embodiment and the 5th embodiment mentioned above the fact that degree of attenuation A(T) of ultrasonic waves due to the round trip in soft tissue Ma is considered, and the fact that the hardware components are almost the same; however it differs from the previous two embodiments in that a pre-measurement routine is executed before executing the main measurement routine for the purpose of diagnosing osteoporosis.

As FIG. 10 shows, in the pre-measurement routine an ultrasonic impulse Ai is radiated toward air (Step SQ12), and the open time echo returned from the end surface of an ultrasonic retarding spacer 1b such as polyethylene bulk, etc., at this time is received by the ultrasonic oscillator 1a (Step SQ13) and the opening time echo level V0 is measured (Step SQ16). After this, the main measurement routine is executed (Step SQ18). In the main measurement routine, processing is executed according to almost the same flow as explained in the 4th embodiment.

In this embodiment the ultrasonic reflection coefficient R of the bone Mb of the examinee relative to soft tissue Ma is given by Equation (21).

$$R=h/[(1+s)\cdot(1-s)\cdot A(T)] \qquad (21)$$

where $$h=-Ve/V0$$

$$s=-Vs/V0$$

Ve: The maximum bone echo level

Vs: The surface echo level when the maximum bone echo level is received

T: The bone echo arrival time when the maximum bone echo is received

A(T) Degree of ultrasonic attenuation when the maximum bone echo level is received V0: The open time echo level Equation (21) is derived as follows.

Firstly, when the sound pressure of the ultrasonic impulse Ai incident on the medium of air from the medium of the ultrasonic wave retarding spacer 1b is Pi, the sound pressure P(0) of the opening echo A0 produced at the interface of the ultrasonic wave retarding spacer 1b and air is given by Equation (22).

$$D0=P(0)/Pi=(Z0-Zc)/(Z0+Zc) \qquad (22)$$

where

Zc: The acoustic impedance of the ultrasonic wave retarding spacer 1b (known)

18

Z0: The acoustic impedance of air

D0: The reflection coefficient of sound pressure at the interface of the ultrasonic wave retarding spacer 1b and air when the ultrasound wave is vertically incident to air from the medium of the ultrasonic wave retarding spacer 1b In this connection, considering the fact that Zc is almost $10^4$ times Z0, Z0/Zc can be taken as tending to 0, so that Equation (23) is obtained from Equation (22).

$$P(0)=-Pi \qquad (23)$$

Below, it is possible to arrive at Equation (21) by following almost the same process as in the 5th embodiment.

Similarly, in this embodiment the impedance Zb of the bone Mb of the examinee is given by Equation (24).

$$Zb=Zc\cdot[(1+s)/(1-s)]\cdot[(1+R)/(1-R)] \qquad (24)$$

where $$s=-Vs/V0$$

The constitution above gives almost the same benefits as mentioned in the 4th embodiment.

In passing, in the 6th embodiment the opening echo level V0 is found by performing a pre-measurement, but the pre-measurement can be omitted when diagnosing if the opening echo level V0 is found at the factory stage and loaded into non-volatile memory such as the ROM, etc.

This invention has been discussed in detail above by using embodiments, but the concrete constitution is not restricted to these embodiments, and any modifications in design that are not beyond the scope of the essence of this invention are also included in this invention. For example, ultrasonic oscillators constituting the transducer are not restricted to thick oscillator types: flexible oscillator types are also possible. Similarly, the central frequency is not restricted to 2.5 MHz. And since the acoustic impedance of soft tissue Ma is close to acoustic impedance of water, the acoustic impedance of water can be used instead of the acoustic impedance of soft tissue Ma in applying Equation (1)

INDUSTRIAL APPLICABILITY

The osteoporosis diagnosing apparatus and method of this invention is suitable for institutions such as hospitals and health centres; in addition to being small and lightweight, the apparatus is easy to operate, and moreover there is no danger of exposure to radiation, so that it is very much preferable for use as equipment for health management in old peoples homes.

What is claimed is:

1. An osteoporosis diagnosing apparatus comprising:

an ultrasonic transducer having a transducer surface for submitting and receiving ultrasonic impulses, said transducer surface adapted to be set on a skin of an examinee and repeatedly radiate ultrasonic impulses from the transducer surface toward a surface of a bone beneath the skin and receive at the transducer surface echos of the radiated ultrasonic impulses reflected at the surface of the bone while a direction of the transducer surface is changed in various directions including a direction perpendicular to the surface of the bone;

an echo level detector which detects echo levels of said echos;

a maximum echo extraction unit which extracts a maximum echo level from the echo levels detected by said echo level detector; and

19 a decision unit which determines that the bone is osteoporosis when a value of said maximum echo level extracted by said maximum echo extraction unit is lower than a predetermined fixed value.

2. An osteoporosis diagnosing apparatus according to claim 1, further comprising:
an output unit which outputs a result determined by said decision unit.

3. An osteoporosis diagnosing apparatus comprising:
an ultrasonic transducer having a transducer surface for emitting and receiving ultrasonic impulses, said transducer surface adapted to be set on a skin of an examinee and repeatedly radiate ultrasonic impulses from the transducer surface toward a surface of a bone beneath the skin and receive at the transducer surface echos of the radiated ultrasonic impulses reflected at the surface of the bone while a direction of the transducer surface is changed in various directions including a direction perpendicular to the surface of the bone;
an echo level detector which detects echo levels of said echos;
a maximum echo extraction unit which extracts a maximum echo level from the echo levels detected by said echo level detector;
a reflection coefficient calculator which calculates an ultrasonic reflection coefficient of the bone relative to soft tissue around the bone on the basis of said maximum echo level; and
a decision unit which determines whether the bone is osteoporosis or not on the basis of the ultrasonic reflection coefficient calculated by said reflection coefficient calculator.

4. An osteoporosis diagnosing apparatus according to claim 3, further comprising:
a timing unit which determines an echo arrival time from a timing at which said ultrasonic transducer radiates the ultrasonic impulse to a timing at which an echo of an ultrasonic impulse is received at said transducer surface, said reflection coefficient calculator calculating the ultrasonic reflection coefficient on the basis of the maximum echo level extracted by said maximum echo extraction unit and the echo arrival time determined by said timing unit.

5. An osteoporosis diagnosing apparatus according to claim 4, wherein said reflection coefficient calculator calculates an attenuation degree of the ultrasonic impulse during a round trip in the soft tissue based on said echo arrival time when the maximum echo level is extracted by said maximum echo extraction unit, and further calculates an acoustic impedance of the bone of the examinee based on said attenuation degree and said maximum echo level.

6. An osteoporosis diagnosing apparatus according to claims 3, 4 or 5, wherein said decision unit determines that the bone is osteoporosis when a value of the ultrasonic reflection coefficient calculated by said reflection coefficient calculator is smaller than a predetermined reference value.

7. An osteoporosis diagnosing apparatus according to claim 3, further comprising:
an output unit which outputs a result determined by said decision unit.

8. An osteoporosis diagnosing apparatus comprising:
an ultrasonic transducer having a transducer surface for emitting and receiving ultrasonic impulses, said transducer surface adapted to be set on a skin of an examinee and repeatedly radiate ultrasonic impulses from the transducer surface toward a surface of a bone beneath

20 the skin and receive at the transducer surface echos of the radiated ultrasonic impulses reflected at the surface of the bone while a direction of the transducer surface is changed in various directions including a direction perpendicular to the surface of the bone;
an echo level detector which detects echo levels of said echos;
a maximum echo extraction unit which extracts a maximum echo level from the echo levels detected by said echo level detector;
an acoustic impedance calculator which calculates an acoustic impedance of the bone based on said maximum echo level extracted by said maximum echo extraction unit; and
a decision unit which determines whether the bone is osteoporosis or not on the basis of the acoustic impedance calculated by said acoustic impedance calculator.

9. An osteoporosis diagnosing apparatus according to claim 8, further comprising:
a timing unit which determines an echo arrival time from a timing at which said ultrasonic transducer radiates the ultrasonic impulse to a timing at which an echo of an ultrasonic impulse is received at said transducer surface, said acoustic impedance calculator calculating said acoustic impedance based on said maximum echo level extracted by said maximum echo extraction unit and said echo arrival time determined by said timing unit.

10. An osteoporosis diagnosing apparatus according to claim 9, wherein said acoustic impedance calculator calculates an attenuation degree of the ultrasonic impulse during a round trip in the soft tissue based on the echo arrival time when the maximum echo level is extracted by said maximum echo extraction unit, and further calculates the acoustic impedance of the bone of the examinee based on said attenuation degree and said maximum echo level.

11. An osteoporosis diagnosing apparatus according to claim 8, wherein said acoustic impedance calculator calculates an ultrasonic reflection coefficient of the bone relative to soft tissue around the bone based on said maximum echo level, and further calculates the acoustic impedance of the bone based on said ultrasonic reflection coefficient.

12. An osteoporosis diagnosing apparatus according to claims 8, 9, 10 or 11, wherein said decision unit determines that the bone is osteoporosis when said acoustic impedance calculated by said acoustic impedance calculator is smaller than a predetermined impedance reference value.

13. An osteoporosis diagnosing apparatus according to claim 8, further comprising:
an output unit which outputs a result determined by said decision unit.

14. An osteoporosis diagnosing apparatus comprising:
an ultrasonic transducer having a transducer surface for emitting and receiving ultrasonic impulses, said transducer surface adapted to be set on a skin of an examinee and repeatedly radiate ultrasonic impulses from the transducer surface toward a surface of a bone beneath the skin and receive at the transducer surface echos of the radiated ultrasonic impulses reflected at the surface of the bone while a direction of the transducer surface is changed in various directions including a direction perpendicular to the surface of the bone;
an analogue digital converter which converts receiving signals of the echos into digital echo signals;
a program memory which stores a processing program which includes a routine for reading said digital echo signals output from said analog digital converter, a routine for detecting echo levels based on the digital echo signals, and a routine for extracting a maximum echo level from the detected echo levels; and a central processing unit which determines that the bone is osteoporosis when a value of said maximum echo level extracted by executing said processing program is lower than a predetermined fixed value.

15. An osteoporosis diagnosing apparatus comprising:

an ultrasonic transducer having a transducer surface for emitting and receiving ultrasonic impulses, said transducer surface adapted to be set on a skin of an examinee and repeatedly radiate ultrasonic impulses from the transducer surface toward a surface of a bone beneath the skin and receive at the transducer surface echos of the radiated ultrasonic impulses reflected at the surface of the bone while a direction of the transducer surface is changed in various directions including a direction perpendicular to the surface of the bone;

an analogue digital converter which converts receiving signals of the echos into digital echo signals;

a program memory which stores a processing program which includes a routine for reading said digital echo signals output from said analog digital converter, a routine for detecting echo levels based on the digital echo signals, a routine for extracting a maximum echo level from the detected echo levels, and a routine for calculating an ultrasonic reflection coefficient of the bone relative to soft tissue around the bone on the basis of said maximum echo level; and a central processing unit which calculates said ultrasonic reflection coefficient by executing said processing program and determines whether the bone is osteoporosis or not based on said ultrasonic reflection coefficient.

16. An osteoporosis diagnosing apparatus according to claim 15, further comprising:

a timing unit which measures an echo arrival time from a timing at which said ultrasonic transducer radiates the ultrasonic impulse to a timing at which an echo of an ultrasonic impulse is received at said transducer surface, said processing program including a procedure which calculates the ultrasonic reflection coefficient based on the maximum echo level and said echo arrival time.

17. An osteoporosis diagnosing apparatus according to claim 16, wherein said program memory further stores as part of said processing program a procedure which calculates an attenuation degree of the ultrasonic impulse during a round trip in the soft tissue based on said echo arrival time when the maximum echo level is received, and a procedure which calculates the ultrasonic reflection coefficient based on said attenuation degree and said maximum echo level.

18. An osteoporosis diagnosing apparatus according to claim 15, 16 or 17, wherein said central processing unit determines that the bone is osteoporosis when a value of said ultrasonic reflection coefficient is smaller than a predetermined reference value.

19. An osteoporosis diagnosing apparatus according to claims 16 or 17, further comprising:

an amplifying circuit system provided between said ultrasonic transducer and said analogue digital transducer, wherein said central processing unit calculates the ultrasonic reflection coefficient based on the following relationship, $$R = Ve/(P*Q*B*Vi*A(T)),$$

where

A(T): Attenuation degree of ultrasound wave during a round trip in the soft tissue, T: Echo arrival time, P: Sound pressure of the ultrasonic impulse output from the transducer surface in the direction perpendicular to the surface of the bone when a unit electrical signal is applied to the transducer, Q: Amplitude of the receiving signals when an echo vertically incidents at the transducer surface, B: Total degree of amplification of the amplifying circuit system, Vi: Amplitude of an electrical signal applied to the ultrasonic transducer, and Ve: Maximum bone echo level.

20. An osteoporosis diagnosing apparatus according to claim 14, wherein said analogue digital converter comprises a rapid access sampling memory which temporarily stores said digital echo signals digitalized in a certain sampling period.

21. An osteoporosis diagnosing apparatus comprising:

an ultrasonic transducer having a transducer surface for emitting and receiving ultrasonic impulses, said transducer surface adapted to be set on a skin of an examinee and repeatedly radiate ultrasonic impulses from the transducer surface toward a surface of a bone beneath the skin and receive at the transducer surface echos of the radiated ultrasonic impulses reflected at the surface of the bone while a direction of the transducer surface is changed in various directions including a direction perpendicular to the surface of the bone;

an analogue digital converter which converts receiving signals of the echos into digital echo signals;

a program memory which stores a processing program which includes a routine for reading said digital echo signals output from said analog digital converter, a routine for detecting echo levels based on the digital echo signals, a routine for extracting a maximum echo level from the detected echo levels, and a routine for calculating an acoustic impedance of the bone based on said extracted maximum echo level; and a central processing unit which calculates the acoustic impedance by executing said processing program and determines whether the bone is osteoporosis based on said acoustic impedance of the bone.

22. An osteoporosis diagnosing apparatus according to claim 21, further comprising:

a timing unit which measures an echo arrival time from a timing at which said ultrasonic transducer radiates the ultrasonic impulse to a timing at which an echo of an ultrasonic impulse is received at said transducer surface, said processing program including a procedure which calculates an ultrasonic reflection coefficient of said bone relative to soft tissue around the bone based on the maximum echo level and said echo arrival time.

23. An osteoporosis diagnosing apparatus according to claim 21, wherein said program memory further stores as part of said processing program a procedure which calculates an attenuation degree of the ultrasonic impulse during a round trip in the soft tissue based on said echo arrival time when the maximum echo level is received, and a procedure which calculates the ultrasonic reflection coefficient based on said attenuation degree and said maximum echo level.

24. An osteoporosis diagnosing apparatus according to claim 21, wherein said program memory further stores as part of said processing program a procedure which calculates said ultrasonic reflection coefficient based on said maximum echo level, and a procedure which calculates the acoustic impedance based on said ultrasonic reflection coefficient.

25. An osteoporosis diagnosing apparatus according to claims 21, 22, 23 or 24, wherein said processing unit determines that the bone is osteoporosis when said acoustic impedance is smaller than a predetermined impedance reference value.

26. An osteoporosis diagnosing apparatus according to claims 15 or 24, wherein said central processing unit calculates the ultrasonic reflection coefficient based on the following relationship, $R = Ve/V0$, where
  Ve: Maximum echo level, and
  V0: Total echo level of an ultrasonic impulse from the ultrasonic transducer.

27. An osteoporosis diagnosing apparatus according to claims 15 or 24, further comprising:
  an amplifying circuit system provided between said ultrasonic transducer and said analogue digital transducer,
  wherein said central processing unit calculates the ultrasonic reflection coefficient based on the following relationship, $$R = Ve/P*Q*B*Vi,$$

where
  P: Sound pressure of the ultrasonic impulse output from the transducer surface in the direction perpendicular to the surface of the bone when a unit electrical signal is applied to the transducer,
  Q: Amplitude of the receiving signals when an echo vertically incidents at the transducer surface,
  B: Total degree of amplification of the amplifying circuit system,
  Vi: Amplitude of an electrical signal applied to the ultrasonic transducer, and
  Ve: Maximum echo level.

28. An osteoporosis diagnosing apparatus according to claims 29, 22 or 23, wherein said central processing unit calculates the acoustic impedance of the bone based on the following relationship, $$Zb = Za(Ve/V0+1)/(1-Ve/V0),$$

where
  Zb: Acoustic impedance of the bone,
  Za: Acoustic impedance of soft tissue or water,
  Ve: Maximum echo level, and
  V0: Total echo level of an ultrasonic impulse radiated from the ultrasonic transducer.

29. An osteoporosis diagnosing apparatus according to claims 21, 22, 23 or 24, wherein said central processing unit calculates the acoustic impedance of the bone based on the following relationship, $$Zb = Za(R+1)/(1-R),$$

where
  Za: Acoustic impedance of soft tissue or water, and
  R: Ultrasonic reflection coefficient of the bone relative to the soft tissue around the bone.

30. An osteoporosis diagnosing apparatus according to claim 14, further comprising:
  a data memory which temporarily memorizes data including said detected echo levels and said maximum echo level,
  wherein said data memory has an area which stores a currently detected echo level and the maximum echo level, and said processing program includes a routine for comparing the currently detected echo level with the maximum echo level and a routine for updating the maximum echo level with the currently detected echo level when the currently detected echo level is greater than the maximum echo level.

31. An osteoporosis diagnosing apparatus according to claim 14, further comprising:
  a data memory which temporarily memorizes data including said detected echo levels and said maximum echo level,
  wherein said data memory has an area which stores all of the echo levels and the maximum echo level detected during a whole detection period by said processing program, and said processing program includes a routine for extracting the maximum echo level from the echo levels stored in said data memory.

32. An osteoporosis diagnosing apparatus according to claim 14, further comprising:
  a data memory which temporarily memorizes data including said detected echo levels and said maximum echo level, said data memory having an area which stores a currently detected echo level and the maximum echo level; and
  a level display which simultaneously displays the currently detected echo level and the maximum echo level.

33. An osteoporosis diagnosing apparatus comprising:
  an ultrasonic transducer including a transducer surface for emitting and receiving ultrasonic impulses and an ultrasonic wave retarding spacer attached to the transducer surface, said ultrasonic transducer adapted to be set on a skin of an examinee at the ultrasonic wave retarding spacer and repeatedly radiate ultrasonic impulses from the transducer surface toward a surface of a bone beneath the skin and receive at the transducer surface a first echo reflected at a surface of the skin and a second echo reflected at the surface of the bone while a direction of the transducer surface is changed in various directions including a direction perpendicular to the surface of the bone;
  an analogue digital converter which converts receiving signals of the first and second echos into first and second digital echo signals;
  a program memory which stores a processing program including a routine which measures an echo arrival time difference between a timing at which the first echo is received at the transducer surface and a timing at which the second echo is received at the transducer surface, a routine which detects first and second echo levels from the first and second digital echo signals, a routine which extracts a maximum echo level from the detected second echo levels, a routine which calculates an ultrasonic reflection coefficient of the bone relative to soft tissue around the bone based on the maximum echo level and the echo arrival time difference; and
  a central processing unit which calculates an ultrasonic reflection coefficient by executing said processing program, and determines whether the bone is osteoporosis based on the ultrasonic reflection coefficient.

34. An osteoporosis diagnosing apparatus according to claim 33, wherein said central processing unit calculates the ultrasonic reflection coefficient based on the following relationship, $$R=((Za+Zc)*(Za-Zc)*Ve)/(4Za*Zc*A(T)*Vs),$$

where
- Zc: Acoustic impedance of the ultrasonic wave retarding spacer,
- Za: Acoustic impedance of soft tissue,
- Ve: Maximum echo level,
- Vs: First echo level when maximum echo level is received,
- T: Echo arrival time difference when maximum echo level is received, and
- A(T): Attenuation degree of ultrasound wave when maximum echo level is received.

35. An osteoporosis diagnosing apparatus comprising:

an ultrasonic transducer including a transducer surface for emitting and receiving ultrasonic impulses and an ultrasonic wave retarding spacer attached to the transducer surface, said ultrasonic transducer adapted to be set on a skin of an examinee at the ultrasonic wave retarding spacer and repeatedly radiate ultrasonic impulses from the transducer surface toward a surface of a bone beneath the skin and receive at the transducer surface a first echo reflected at a surface of the skin and a second echo reflected at the surface of the bone while a direction of the transducer surface is changed in various directions including a direction perpendicular to the surface of the bone;

an analogue digital converter which converts receiving signals of the first and second echos into first and second digital echo signals;

a program memory which stores a processing program including a routine which measures an echo arrival time difference between a timing at which the first echo is received at the transducer surface and a timing at which the second echo is received at the transducer surface, a routine which detects first and second echo levels from the first and second digital echo signals, a routine which extracts a maximum echo level from the detected second echo levels, a routine which calculates an acoustic impedance of the bone based on the maximum echo level and the echo arrival time difference; and a central processing unit which calculates the acoustic impedance by executing said processing program, and determines whether the bone is osteoporosis based on the acoustic impedance.

36. An osteoporosis diagnosing apparatus according to claim 35, wherein said program memory further stores as part of said processing program a routine which calculates an ultrasonic reflection coefficient of the bone relative to soft tissue around the bone based on said maximum echo level, said first echo level and said echo arrival time difference, and a routine which calculates said acoustic impedance of the bone based on said ultrasonic reflection coefficient.

37. An osteoporosis diagnosing apparatus according to claim 36, wherein said central processing unit calculates the acoustic impedance of the bone based on the following relationship, $$Zb=Zc*((1+s)/(1-s))*((1+R)/(1-R)),$$

where
- s=−Vs/V0,
- V0: Echo level returned from an end surface of the ultrasonic wave retarding spacer when an ultrasonic impulse is radiated toward air,
- R: Ultrasonic reflection coefficient of the bone relative to the soft tissue around the bone, and
- Zc: Acoustic impedance of the ultrasonic wave retarding spacer.

38. An osteoporosis diagnosing apparatus comprising:

an ultrasonic transducer including a transducer surface for emitting and receiving ultrasonic impulses and an ultrasonic wave retarding spacer attached to the transducer surface, said ultrasonic transducer adapted to be set on a skin of an examinee at the ultrasonic wave retarding spacer and repeatedly radiate ultrasonic impulses from the transducer surface toward a surface of a bone beneath the skin and receive at the transducer surface a first echo reflected at a surface of the skin and a second echo reflected at the surface of the bone while a direction of the transducer surface is changed in various directions including a direction perpendicular to the surface of the bone;

an analogue digital converter which converts receiving signals of the first and second echos into first and second digital echo signals;

a premeasurement program having a routine which determines an open time echo level when an ultrasonic impulse is radiated towards air and when an open time echo from an end of said ultrasonic wave retarding spacer is received by said ultrasonic oscillator;

a main measurement program having a routine which measures an echo arrival time difference between a timing at which the first echo is received at the transducer surface and a timing at which the second echo is received at the transducer surface, a routine which detects first and second echo levels from the first and second digital echo signals, a routine which extracts a maximum echo level from the detected second echo levels, a routine which calculates an ultrasonic reflection coefficient of the bone relative to soft tissue around the bone based on the maximum echo level, the first echo level, and the echo arrival time difference;

a program memory which stores said premeasurement program and said main measurement program; and a central processing unit which calculates an ultrasonic reflection coefficient by executing said main measurement program, and determines whether the bone is osteoporosis based on the ultrasonic reflection coefficient.

39. An osteoporosis diagnosing apparatus according to claim 38, wherein said central processing unit calculates the ultrasonic reflection coefficient based on the following relationship, $$R=h/((1+s)*(1-s)*A(T)),$$

where
- h=−Ve/V0,
- s=−Vs/V0,
- Ve: Maximum echo level,
- Vs: First echo level when maximum bone echo level is received,
- T: Bone echo arrival time difference when maximum bone echo level is received,
- A(T): Attenuation degree of ultrasound wave when maximum bone echo level is received, and
- V0: Open time echo level.

40. An osteoporosis diagnosing apparatus comprising:

an ultrasonic transducer including a transducer surface for emitting and receiving ultrasonic impulses and an ultrasonic wave retarding spacer attached to the transducer surface, said ultrasonic transducer adapted to be set on a skin of an examinee at the ultrasonic wave retarding spacer and repeatedly radiate ultrasonic impulses from the transducer surface toward a surface of a bone beneath the skin and receive at the transducer surface a first echo reflected at a surface of the skin and a second echo reflected at the surface of the bone while a direction of the transducer surface is changed in various directions including a direction perpendicular to the surface of the bone;

an analogue digital converter which converts receiving signals of the first and second echos into first and second digital echo signals;

a program memory which stores a main measurement program having a routine which measures an echo arrival time difference between a timing at which the first echo is received at the transducer surface and a timing at which the second echo is received at the transducer surface, a routine which detects first and second echo levels from the first and second digital echo signals, a routine which extracts a maximum echo level from the detected second echo levels, a routine which calculates an ultrasonic reflection coefficient of the bone relative to soft tissue around the bone based on the maximum echo level, the first echo level, and the echo arrival time difference, and a routine which calculates the acoustic impedance of the bone based on said ultrasonic reflection coefficient; and a central processing unit which calculates said acoustic impedance by executing said main measurement program, and determines whether the bone is osteoporosis based on said acoustic impedance.

41. An osteoporosis diagnosing apparatus according to claim 40, wherein said central processing unit calculates the acoustic impedance of the bone based on the following relationship, $$Zb=Zc*((1+s)/(1-s))*((1+R)/(1-R)),$$

where
s=−VS/V0,
V0: Open echo level,
R: Ultrasonic reflection coefficient of the bone relative to the soft tissue around the bone, and
Zc: Acoustic impedance of the ultrasonic wave retarding spacer.

42. An osteoporosis diagnosing method comprising the steps of:

setting an ultrasonic transducer on a skin of an examinee;

repeatedly radiating ultrasonic impulses from a transducer surface of said ultrasonic transducer toward a surface of a bone beneath the skin while a direction of the transducer surface is changed in various directions including a direction perpendicular to the surface of the bone;

receiving at the transducer surface echos of the radiated ultrasonic impulses reflected the surface of the bone;

measuring echo levels of said echos;

determining a maximum echo level from the measured echo levels;

estimating a bone density or bone elastic modulus based on said maximum echo level;

calculating an ultrasonic reflection coefficient of the bone relative to soft tissue around the bone on the basis of said maximum echo level; and determining whether the bone is osteoporosis on the basis of said ultrasonic reflection coefficient.

43. An osteoporosis diagnosing method comprising the steps of:

setting an ultrasonic transducer on a skin of an examinee;

repeatedly radiating ultrasonic impulses from a transducer surface of said ultrasonic transducer toward a surface of a bone beneath the skin while a direction of the transducer surface is changed in various directions including a direction perpendicular to the surface of the bone;

receiving at the transducer surface echos of the radiated ultrasonic impulses reflected the surface of the bone;

measuring echo levels of said echos;

determining a maximum echo level from the measured echo levels;

estimating a bone density or bone elastic modulus based on said maximum echo level;

calculating an acoustic impedance of the bone on the basis of said maximum echo level; and determining whether the bone is osteoporosis on the basis of said acoustic impedance.

44. An osteoporosis diagnosing method according to claim 43, further comprising:

a step of calculating an ultrasonic reflection coefficient of the bone relative to soft tissue around the bone on the basis of said maximum echo level, wherein the step of calculating said acoustic impedance is performed on the basis of said ultrasonic reflection coefficient.

* * * * *